US010423274B2

(12) United States Patent
Cohen et al.

(10) Patent No.: US 10,423,274 B2
(45) Date of Patent: *Sep. 24, 2019

(54) TOUCH INPUT DEVICE WITH PATHOGEN TRANSMISSION MITIGATION

(71) Applicant: International Business Machines Corporation, Armonk, NY (US)

(72) Inventors: Guy Cohen, Mohegan Lake, NY (US); James R. Kozloski, New Fairfield, CT (US); Clifford A. Pickover, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/027,841

(22) Filed: Jul. 5, 2018

(65) Prior Publication Data

US 2018/0321790 A1 Nov. 8, 2018

Related U.S. Application Data

(60) Continuation of application No. 15/198,174, filed on Jun. 30, 2016, now Pat. No. 10,042,466, which is a
(Continued)

(51) Int. Cl.
*G06F 3/041* (2006.01)
*A61L 2/10* (2006.01)
(Continued)

(52) U.S. Cl.
CPC ............. *G06F 3/0416* (2013.01); *A61L 2/10* (2013.01); *A61L 2/24* (2013.01); *G06F 3/017* (2013.01);
(Continued)

(58) Field of Classification Search
CPC .... G06F 3/0416; G06F 3/017; G06F 3/03545; G06F 3/0418; G06F 3/0421; G06F 3/044;
(Continued)

(56) References Cited

U.S. PATENT DOCUMENTS 6,458,331 B1 10/2002 Roberts
6,490,351 B1 12/2002 Roberts
(Continued)

OTHER PUBLICATIONS

Robinson, B., "Sanitize Your Cell Phone With Ultraviolet Light", http://mashable.com/2010/10/19/uv-cellphone-sterilizer/#Miuf7JPEMZqh, Oct. 18, 2010, p. 1.
(Continued)

*Primary Examiner* — Jennifer Mehmood
*Assistant Examiner* — Ngan T Pham Lu
(74) *Attorney, Agent, or Firm* — Fleit Gibbons Gutman Bongini Bianco PL; Jose Gutman

(57) ABSTRACT

Methods, device, and computer program product for mitigating pathogen transmission via a touch surface of a touch input device. Mitigation is accomplished through selective touch surface sterilization and through touchscreen user interface reorganization. The touch surface includes a pixel array for illuminating selected portions of the touch surface with ultraviolet light of a sterilization wavelength based upon the received touch inputs. The selective illumination may occur while receiving a touch input or after an accumulation of touch inputs have been received. The user interface may also be reorganized based on received touch inputs in order to locate user interface icons to lesser touched locations of the touch surface.

20 Claims, 10 Drawing Sheets

Related U.S. Application Data division of application No. 14/204,894, filed on Mar. 11, 2014, now Pat. No. 10,156,922.

(51) Int. Cl.
| | |
|---|---|
| *G06F 3/01* | (2006.01) |
| *G06F 3/0488* | (2013.01) |
| *G06F 3/042* | (2006.01) |
| *G06F 3/0481* | (2013.01) |
| *G06F 3/044* | (2006.01) |
| *A61L 2/24* | (2006.01) |
| *G06F 3/0354* | (2013.01) |
| *G06F 3/0484* | (2013.01) |

(52) U.S. Cl.
CPC .......... *G06F 3/03545* (2013.01); *G06F 3/044* (2013.01); *G06F 3/0418* (2013.01); *G06F 3/0421* (2013.01); *G06F 3/0481* (2013.01); *G06F 3/0488* (2013.01); *G06F 3/04817* (2013.01); *G06F 3/04845* (2013.01); *G06F 3/04883* (2013.01); *H05K 999/99* (2013.01); *A61L 2202/16* (2013.01); *G06F 2203/04106* (2013.01)

(58) Field of Classification Search
CPC ............... G06F 3/0481; G06F 3/04817; G06F 3/04845; G06F 3/0488; G06F 3/04883; G06F 2203/04106; A61L 2/10; A61L 2/24; A61L 2202/16; H05K 999/99
USPC ........................................................ 345/173
See application file for complete search history.

(56) References Cited

U.S. PATENT DOCUMENTS

| | | | |
|---|---|---|---|
| 7,431,848 | B2 | 10/2008 | James |
| 8,296,493 | B1 | 10/2012 | EngelHardt et al. |
| 8,354,663 | B2 | 1/2013 | Adivarahan et al. |
| 8,431,910 | B1 | 4/2013 | Perry |
| 2006/0188389 | A1 | 8/2006 | Levy |
| 2007/0258852 | A1 | 11/2007 | Hootsmans et al. |
| 2009/0257912 | A1 | 10/2009 | Lane et al. |
| 2011/0256019 | A1* | 10/2011 | Gruen ................ A61L 2/10 422/24 |
| 2011/0291995 | A1 | 12/2011 | Shr et al. |
| 2012/0206373 | A1* | 8/2012 | Van Eerd ............ G06F 3/04883 345/173 |
| 2013/0016752 | A1 | 1/2013 | Lell et al. |
| 2013/0045132 | A1 | 2/2013 | Tumanov |
| 2013/0062534 | A1 | 3/2013 | Cole |

OTHER PUBLICATIONS

Wikipedia, "Methicillin-resistant *Staphylococcus aureus*", https://en.wikipedia.org/wiki/Methicillin-resistant_Staphylococcus_aureus, last visited on May 27, 2016, pp. 1-12.

Hendrick, B., "MRSA Strain on the Rise in Hospitals", http://www.webmd.com/skin-problems-and-treatments/news/20091124/mrsa-strain-on-the-rise-in-hospitals, Nov. 24, 2009, pp. 1-4.

Kramer, A., et al., "How long do nosocomial pathogens persist on inanimate surfaces? A systematic review", http://www.biomedcentral.com/1471-2334/6/130, Aug. 16, 2006, pp. 1-10.

Porter, C., "Calling all Germs", http://www.wsj.com/articles/SB10000872396390444868204578064960544587522, Oct. 23, 2012, pp. 1-7.

Riley, D.J., et al., "An in-vitro study of the sterilization of titanium dental implants using low intensity UV-radiation", Dental Materials, Jan. 20, 2005, pp. 1-5, vol. 21.

Spectroline, "The World Leader in Ultraviolet & Leak Detection Technology", redirected from www.cellblaster.com to http://www.spectroline.com, last visited on Jun. 7, 2016, pp. 1-3.

Non-Final Office Action dated Jun. 1, 2016, received for U.S. Appl. No. 14/204,894.

Kowalski, W., et al., "UVGI Design Basics for Air and Surface Disinfection," Heating/Piping/Air Conditioning Engineering, Jan. 2000, pp. 100-110. vol. 72, No. 1.

Shahaby, A.F., et al., "Mobile Phone as Potential Reservoirs of Bacterial Pathogens," African Journal of Biotechnology, Nov. 2012, pp. 15896-15904, vol. 11. No. 92. Available online at http://www.academicjournals.org/AJB, DOI: 10.5897/AJB12.1836, ISSN 1684-5315, Copyright 2012 Academic Journals.

* cited by examiner

| | A | B | C | D |
|---|---|---|---|---|
| 1 | 65-92<br>240-121 | 3-2<br>35-33 | 3-2<br>60-15 | 3-2<br>22-4 |
| 2 | 3-2<br>12-66 | 3-2<br>12-66 | 3-2<br>12-66 | 3-2<br>12-66 |
| 3 | 125-321<br>12-66 | 88-55<br>12-66 | 3-2<br>16-66 | 42-50<br>12-66 |
| 4 | 3-2<br>115-66 | 3-2<br>112-69 | 3-2<br>102-74 | 3-2<br>127-64 |

TOUCH INPUT DEVICE WITH PATHOGEN TRANSMISSION MITIGATION

BACKGROUND

This disclosure relates to mitigating infectious consequences of microorganisms present on computer touch surfaces such as touchpads and touchscreens, and more specifically, to methods and systems for user interface reorganization and selective touch input sterilization for mitigating transmission of pathogens between computer operators.

Touch input devices such as touchpads and touchscreens are an important user interface component on many computer based devices. Touchpads are popular on laptops as an alternative to a mouse, and touchscreens can be found on devices including cell phones, tablets, laptops, personal computers, kiosks, and gaming systems. Due to frequent touching, pathogens can be found on touch surfaces used to interface with computer based systems. Thus, touch input devices can become a mechanism for spreading diseases between human operators of computers.

Pathogens, including bacterium, prion, fungus and virus are known to survive in environments including touch input surfaces. Most gram-positive bacteria, such as *Enterococcus* spp. (including VRE), *Staphylococcus aureus* (including MRSA), or *Streptococcus pyogenes*, survive for months on dry surfaces. Many gram-negative species, such as *Acinetobacter* spp., *Escherichia coli*, *Klebsiella* spp., *Pseudomonas aeruginosa*, *Serratia marcescens*, or *Shigella* spp., can also survive for months. A few others, such as *Bordetella pertussis*, *Haemophilus influenzae*, *Proteus vulgaris*, or *Vibrio cholerae*, can persist for days. *Mycobacterium tuberculosis*, and spore-forming bacteria, including *Clostridium difficile*, can also survive for months on surfaces. *Candida albicans* as the most important nosocomial fungal pathogen can survive up to four months on surfaces. Persistence of other yeasts, such as *Torulopsis glabrata*, was described to be five months or shorter. *Candida parapsilosis* can survive for fourteen days. Most viruses from the respiratory tract, such as corona, coxsackie, influenza, SARS or rhino virus, can persist on surfaces for a few days. Viruses from the gastrointestinal tract, such as astrovirus, HAV, polio- or rota virus, persist for approximately two months. Blood-borne viruses, such as HBV or HIV, can persist for more than one week. Herpes viruses, such as CMV or HSV type one and two, have been shown to persist from only a few hours up to seven days. The most common nosocomial pathogens can well survive or persist on surfaces for months and can thereby be a continuous source of transmission if no regular preventive surface disinfection is performed. A first computer operator's finger can deposit any of a number of pathogens on a computer's touch input surface and a second computer operator's finger can receive the pathogen when using the touch input surface sometime during the life of the pathogens, thereby providing a mechanism for spreading disease.

Touch input surface sterilization using a chemical disinfectant can mitigate disease spreading. However, cleaning a touch surface with a chemical disinfectant may also damage the touch input surface functionality of the surface. Powerful chemical disinfectants can harm a touch surface, including producing a delamination of touch surface materials and a degradation of optical characteristics of the touch surface. Chemical disinfectants are also inconvenient because a supply inventory of such chemicals needs to be kept available for use on the touch input surface. Also, touch surface cleaning maintenance is manual process and may be perceived as an inconvenience or a nuisance if and when an operator remembers to clean their device. Furthermore, such cleaning may not occur frequently enough for adequate sterilization.

Radiating pathogens with ultraviolet light of a sterilization wavelength can also mitigate the spreading of a disease to a computer operator. While ultraviolet sterilization eliminates a need for disinfectant chemicals, it however has the potential to expose a computer operator to undesirable ultraviolet radiation. Furthermore, generally radiating the area of a touch surface with of ultraviolet radiation may consume excessive power. Power conservation is an important component in battery operated devices such as cell phones, tablets and personal computers.

Touchscreen based user interfaces locate icons on the touchscreen that are activated when touched by computer operators. Thus, computer operators touch certain areas of a touchscreen more than other areas due to the user interface. If a touchscreen is not sterilized, pathogens are more likely present in areas of the touchscreen that are most often touched. Consequently, such user interfaces do not mitigate transmission of pathogens to computer operators.

BRIEF SUMMARY

According to one example, a method comprises: determining, with a controller, that a touch input has been received at a touch location on a touch surface; selecting, with the controller and based upon the touch location, a portion of the touch surface for illumination with ultraviolet light of a sterilization wavelength from at least one pixel of an ultraviolet pixel array comprising a plurality of pixels that are individually selectable by the controller, the selected portion being selected to include the touch location; selecting to activate the at least one pixel which is less than the plurality of pixels, and to deactivate the remaining pixels in the plurality of pixels conserving power of a device, to thereby generate with the activated at least one pixel ultraviolet light of a sterilization wavelength to illuminate the selected portion of the touch surface; and illuminating, by the activated at least one pixel of the ultraviolet pixel array where each pixel of the array is configured to illuminate a portion of the touch surface, the selected portion of the touch surface with an ultraviolet light of a sterilization wavelength.

In accordance with an example, a method comprises receiving a touch input at a touch location on a touch surface, selecting a portion of the touch surface based upon the touch location, and illuminating the portion with an ultraviolet light of a sterilization wavelength. The illuminating may occur during the receiving of the touch input, and may modulate at least one of illumination luminosity and illumination duration of the portion during the receiving of the touch input. The method may further illuminate the portion of the touch surface upon determining an absence of an observer potentially able to view or otherwise be exposed to the ultraviolet light. The touch input is received for a touch duration, and the illuminating modulates at least one of an illumination luminosity and an illumination duration of the portion based upon the touch duration. The method may also comprise receiving an atmospheric condition signal, a personal health condition signal, and/or a public health condition signal wherein the illuminating modulates at least one of an illumination luminosity and an illumination duration of the portion in response. The touch input may be a swipe gesture having a plurality of touch locations; the selecting selects a plurality of portions of the touch surface based upon the plurality of touch locations, and the illuminating illuminates the plurality portions. The swipe gesture may result in receiving the touch input at a first of the plurality of touch locations for a first duration and a second of the plurality of touch locations for a second duration, then the selecting selects a first of the plurality of portions based upon the first of the plurality of touch locations and selects a second of the plurality of portions based upon the second of the plurality of touch locations, and the illuminating modulates at least one of an illumination luminosity and an illumination duration of the first of the plurality of portions based upon the first duration, and modulates at least one of an illumination luminosity and an illumination duration of the second of the plurality of portions based upon the second duration. In another example, the receiving accumulates a plurality of touch inputs having a plurality of touch locations on the touch surface, the selecting selects a plurality of portions of the touch surface based upon the plurality of touch locations, and the illuminating illuminates the plurality of portions. In this example, the receiving accumulates the plurality of touch inputs at a first touch location for a first accumulated duration and a second touch location for a second accumulated duration, the selecting selects a first of the plurality of portions based upon the first of the plurality of touch locations and selects a second of the plurality of portions based upon the second of the plurality of touch locations, and the illuminating modulates at least one of an illumination luminosity and an illumination duration of the first of the plurality of portions based upon the first accumulated duration, and modulates at least one of an illumination luminosity and an illumination duration of the second of the plurality of portions based upon the second accumulated duration. The touch surface may be included within a touchscreen having an active display, or within a touchpad having a static display. In another example, the method includes receiving a peer sterilization signal indicative of a peer touch input received at a peer touch location on a peer touch surface; and receiving an alignment signal indicating that the touch surface is aligned with the peer touch surface, wherein the selecting selects a portion of the peer touch surface based upon the peer touch location and the alignment signal, and the illuminating illuminates the portion of the peer touch surface with the ultraviolet light.

In another example, a device comprises a touch surface for receiving a touch input at a touch location, an ultraviolet pixel array, each pixel of the array configured to illuminate a portion of the touch surface with an ultraviolet light of a sterilization wavelength, and a controller for selecting an at least one pixel of the pixel array for illuminating a selected portion of the touch surface based upon the touch location. A plurality of touch inputs having a plurality of touch locations may be received on the touch surface, the device further comprises an accumulator of accumulating the plurality of touch locations, and an observer absence detector for determining an absence of an observer able to view or otherwise be exposed to the ultraviolet light, and further wherein the controller selects a plurality of pixels of the array for illuminating a plurality of portions of the touch surface based upon the plurality of touch locations, and the controller activates the plurality of pixels based upon the observer absence detector determining the absence of an observer able to view or otherwise be exposed to the ultraviolet light. The plurality of touch inputs are received at a first touch location for a first accumulated duration and a second touch location for a second accumulated duration, the controller selects a first of the plurality of portions based upon the first of the plurality of touch locations and selects a second of the plurality of portions based upon the second of the plurality of touch locations, and the controller modulates at least one of an illumination luminosity and an illumination duration of the first of the plurality of portions based upon the first accumulated duration, and modulates at least one of an illumination luminosity and an illumination duration of the second of the plurality of portions based upon the second accumulated duration.

In another example, a computer program product comprises a storage medium readable by a processing circuit and storing instructions for execution by the processing circuit for performing a method comprising receiving an input signal indicative of a touch input at a touch location on a touch surface, selecting a portion of the touch surface based upon the touch location, and generating an illumination signal for illuminating the portion of the touch surface with an ultraviolet light of a sterilization wavelength. The receiving receives the input signal as a swipe gesture having a plurality of touch locations, the swipe gesture occurs at a first of the plurality of touch locations for a first duration and occurs at a second of the plurality of touch locations for a second duration, the selecting selects a first of a plurality of portions of the touch surface based upon the first of the plurality of touch locations and selects a second of the plurality of portions based upon the second of the plurality of touch locations, and the generating generates the illumination signal for modulating least one of an illumination luminosity and an illumination duration of the first of the plurality of portions based upon the first duration, and for modulating least one of an illumination luminosity and an illumination duration of the second of the plurality of portions based upon the second duration.

In another example, a method comprises accumulating touch inputs and corresponding touch locations received on a touchscreen, analyzing the accumulation to determine an at least one lesser touched location on the touchscreen, and rendering a user interface icon at a location on the touchscreen based upon the analysis. The he method further comprises receiving a sterilization signal indicative of a sterilization of the touchscreen, and initializing the accumulation based upon the receiving. The touch inputs include finger inputs and stylus inputs, the accumulating separately accumulates finger inputs and corresponding finger input locations and stylus inputs and corresponding stylus input locations, the analyzing determines the at least one lesser touched location based upon the accumulation of finger inputs and stylus inputs; and the initializing initializes the accumulation of finger inputs and corresponding finger input locations and maintains the accumulation of stylus inputs and corresponding stylus input locations. The method further comprises determining that a threshold has been reached based upon the accumulating of touch inputs and corresponding touch locations, wherein the rendering renders the user interface icon further based upon the determining of the threshold. The method further comprises determining that a threshold has been reached based upon the accumulating of touch inputs and corresponding touch locations; and activating an ultraviolet light source to emit ultraviolet light of a sterilization wavelength upon the touchscreen based upon the determining of the threshold. The touch inputs include finger inputs and stylus inputs, the accumulating separately accumulates finger inputs and corresponding finger input locations and stylus inputs and corresponding stylus input locations, and the determining determines the threshold based upon the accumulation of finger inputs and corresponding finger input locations. The method further comprises receiving a public health condition signal and or an atmospheric condition signal and determining that a threshold has been reached based upon the public health condition signal and/or the atmospheric condition signal and the accumulating of touch inputs and corresponding touch locations, wherein the rendering renders the user interface further based upon the determining of the threshold. Further, the analyzing determines a plurality of lesser touched locations on the touchscreen and the method further comprises organizing a user interface having a plurality of icons, including the user interface icon, for rendering at first locations on the touchscreen and a plurality of information fields for rendering at a second locations on the touchscreen, and reorganizing the user interface based upon the analyzing, and further wherein the rendering renders the reorganized user interface on the touchscreen. The reorganized user interface locates at least one of the plurality of icons at one of the second locations and at least one of the plurality of information fields at one of the first locations. The method further comprises determining an absence of an operator providing touch inputs on the touchscreen, wherein the rendering renders the reorganized user interface based upon the determined absence. The user interface includes a plurality of screens, each screen display including at least one of the plurality icons, wherein the reorganizing reorganizes the plurality of icons on the plurality of screens of the user interface, and the rendering renders one of the reorganized plurality of screens and renders another of the reorganized plurality of screens in response a touch input received on the touchscreen.

In another example, a device comprises a touchscreen for receiving touch inputs and corresponding touch locations, an accumulator for accumulating touch inputs and corresponding touch locations, a user interface reorganizing module for analyzing the accumulated touch inputs and corresponding touch locations, determining, based on the analyzing, an at least one lesser touched location on the touchscreen, and locating a user interface icon based upon the at least one lesser touched location, and a controller for rendering the user interface icon on the touchscreen based upon the locating. The device may further comprise a receiver for receiving at least one of an atmospheric condition signal and a public health condition signal, wherein the controller further determines that a threshold has been reached based upon the accumulated touch inputs and corresponding touch locations and at least one of the atmospheric condition signal and the public health condition signal, and renders the user interface icon on the touchscreen further based upon the determining of the threshold. The device may further comprise an ultraviolet light source for illuminating the touchscreen with an ultraviolet light of a sterilization wavelength, wherein the controller activates the ultraviolet light source based upon the accumulator. The touch inputs include finger inputs and stylus inputs, and the device further comprises a stylus for entering a second plurality of touch inputs at corresponding touch location on the touchscreen, and the accumulator includes a finger input accumulator for accumulating finger inputs and corresponding finger input locations, and a stylus input accumulator for accumulating stylus inputs and corresponding stylus input locations, and wherein the user interface reorganizing module analyzes both the finger input accumulator and the stylus input accumulator, and the controller initializes the finger input accumulator and maintains the stylus input accumulator based on the activation of the ultraviolet light source. The touch inputs include finger inputs and stylus inputs, the device further comprises a receiver for receiving a sterilization signal indicative of touchscreen sterilization, and a stylus for entering a second plurality of touch inputs and correspond touch location on the touchscreen, and the accumulator includes a finger input accumulator for accumulating finger inputs and corresponding finger input locations and a stylus input accumulator for accumulating stylus inputs and corresponding stylus input locations, and wherein the user interface reorganizing module analyzes both the finger input accumulator and the stylus input accumulator, and the controller initializes the finger input accumulator and maintains the stylus input accumulator based upon the sterilization signal.

In another example, a computer program product comprises a storage medium readable by a processing circuit and storing instructions for execution by the processing circuit for performing a method comprising accumulating signals indicative of touch inputs and corresponding touch locations received on a touchscreen, analyzing the accumulation to determine an at least one lesser touched location on the touchscreen, and generating a rendering signal rendering a user interface icon at a location on the touchscreen based upon the analysis.

BRIEF DESCRIPTION OF THE SEVERAL VIEWS OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present invention, in which.

DETAILED DESCRIPTION

In the following discussion, a great amount of concrete details are provided to help thoroughly understand the present disclosure. However, it is apparent to those of ordinary skill in the art that even though there are no such concrete details, the understanding of the present disclosure would not be influenced. In addition, it should be further appreciated that any specific terms used below are only for the convenience of description, and thus the present disclosure should not be limited to only use in any specific applications represented and/or implied by such terms.

Figure 1:
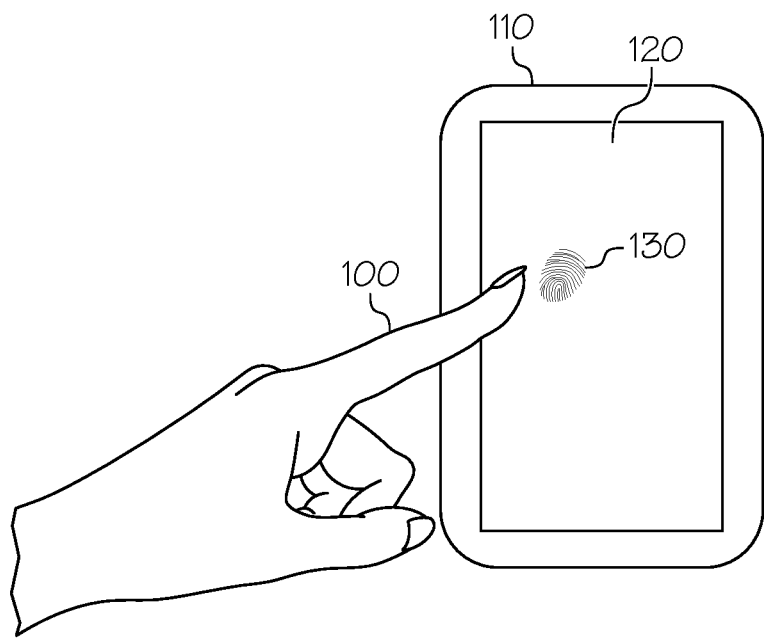
FIG. 1 illustrates an example of an operator having touched a touch input device.

FIG. 1 illustrates an example of an operator having touched a touch input device. The finger 100 of the operator has touched or made a tactile contact with a device 110 having a touch input surface 120 such as a touch screen at a touch location 130, shown as a finger print. The device may be any touch input device including a cell phone, tablet, personal computer with a touchscreen or touchpad, kiosk, point of sale system, and gaming system. Upon touching the touch input, the operator's finger has potentially transferred pathogens to the touch input surface at touch location 130. A subsequent touch at touch location 130 may result in the pathogens being spread to another operator, thereby transmitting the pathogen and providing a mechanism for spreading disease.

Although FIG. 1 shows a single touch by a single operator. Those familiar with touch input devices should appreciate that the touch may be a swipe gesture spanning multiple touch locations, also a touch input surface may accumulate multiple touches by a single operator or single or multiple touch inputs by multiple operators. Each touch potentially deposits an operator's pathogens on the touch input surface, or transferring pathogens from the touch input surface to the operator, or both, thereby transmitting pathogens and providing a mechanism for spreading disease.

Figure 2:
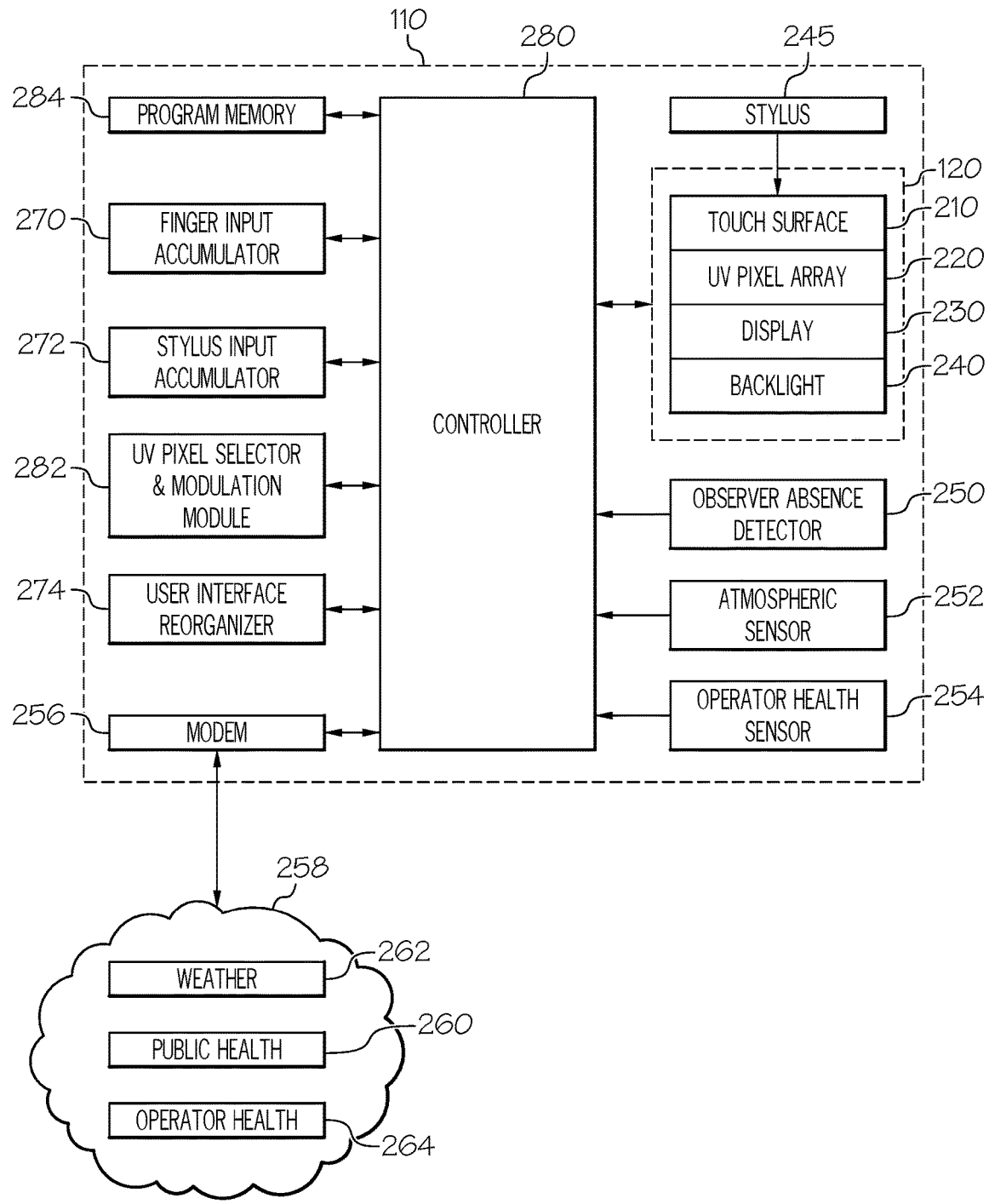
FIG. 2 illustrates an example block diagram of a touch input device capable of pathogen transmission mitigation using selective touch area sterilization and user interface reorganization.

FIG. 2 shows an example block diagram of a touch input device capable of pathogen transmission mitigation using selective touch area sterilization and user interface reorganization. Device 110 has a touch input surface 120 which in this example is a touchscreen. The touch input device has a touch sensor or touch surface 210 for receiving a touch input at a touch location and generating an input signal indicative of the touch input at the touch location. In one example touch surface 210 is part of a capacitive touch input system known to those familiar with the art. Touch surface 210 is not limited to capacitive touch input systems and can also be implemented with other touch based systems including resistive, optical, infrared, radio frequency and acoustic based touch systems know to those familiar with the art.

Selective illumination layer 220 allows selective illumination of the touch surface with ultraviolet light of a sterilization wavelength. In one example, selective illumination layer 220 is an ultraviolet light source that includes an ultraviolet pixel array receiving an illumination signal illuminating a portion of the touch surface with ultraviolet light of a sterilization wavelength. The pixel array is embedded in the touch surface assembly and each pixel of the array is configured to illuminate a portion of the touch surface with an ultraviolet light of a sterilization wavelength. In this example, each pixel is a gallium nitride (GaN) based emitter diode embedded as a thin film layer adjacent to touch surface 210. The GaN sterilizing pixelized source diodes are fabricated to produce a specific wavelength of ultraviolet light, and the film layer including the GaN diode pixel array is effectively transparent to visible light. The wavelength of the GaN based emitter may be tuned by adding indium (In) or aluminum (Al) to the GaN binary crystal. Adding indium shifts the wavelength towards the red while adding aluminum yields a blue shift. For example, by forming a ternary of $Al_xGa_{1-x}N$ with $0<x<1$ it is possible to tune the wavelength from 387 nm (x=0) to 206 nm (x=1).

Those skilled in the art of sterilization have determined that 264 nm is a useful sterilization wavelength, which corresponds to 4.70 eV. An ultraviolet radiation intensity or illumination of 49 $\mu W\ cm^{-2}$ kills bacteria at a rate of approximately 650 million per $cm^2$ of a surface per minute, also 1 eV=2.6702941E-12 (where the number "XEY" is X times ten to the power of Y) watt minutes. Therefore, as an example of a sample calculation, a bacterium is killed at optimal illumination at a rate of 6E6 photons/bacterium= (49E-6 watt minute/$cm^2$)*(1 $cm^2$/6.5E8 bacteria)*(1 eV/2.6702941E-21 watt minute)*(1 photon @ 264 nm/4.7 eV). Alternately, Lambda=264 nm or E_hv=1.24/0.264=4.7 eV=4.7*1.6E-19 Joule (note: q=electron charge=1.6E-19 coulombs). A given illumination luminosity or light intensity of I=49 $uW*cm^{-2}$ kills bacteria at a rate R=650E6 (bacteria/$cm^2$/min)=650E6/60 (bacteria/$cm^2$/sec)=1.0833E7 (bacteria/$cm^2$/sec). The number of photons for intensity I is N_ph=I/(E_hv*q)=49E-6/(4.7*1.6E-19)=6.516E13 photons/sec/$cm^2$. The number of photons to kill one bacteria=6.516E13/1.0833E7=6.015E6 photons. In a light emitting diode (LED) pixel each photon is generated by one electron-hole recombination. So the number of photons in this case is also the amount of electron (charge) needed to take from a battery of a battery operated device.

If the touch surface 210 is included within a touchscreen display, then a display layer 230 and backlight illumination layer 240 are provided to produce an active display for displaying user interface icons and information on the touchscreen as is known to those familiar with touchscreens. In one example, display layer 230 includes a liquid crystal display and backlight illumination layer 240 includes an electroluminescence backlight. In other examples, other display and backlighting technologies art may be used while remaining within the scope of this description. Other technologies known to those familiar with the art include light emitting diode, organic light emitting diode, plasma, field emissive and cathode ray tube display technologies. Furthermore reflective displays which require external illumination such as e-ink displays may also be used with this invention, in such an example, backlight illumination layer

240 could be eliminated. In other examples, the selective illumination layer 220 may be interposed between the backlight layer 240 and the LCD 230, or may integrated into the backlight layer itself. In yet another embodiment the UV pixel array 220 and the backlight 240 can be combined to emit at the visible light for illumination or at UV light for sterilization based on the applied voltage polarity.

If the touch surface of FIG. 2 is included within a touchpad, then layers 230 and 240 can be combined into a static display comprise of an opaque material having a color and optional markings known to those familiar with touchpads.

The device also includes a stylus 245 for interfacing with the touch. The stylus may be an active or a passive stylus for interfacing with any of a variety of touch surface technologies in a manner known to those familiar with the art.

The device also has an observer absence detector 250 for determining an absence of an observer able to be exposed to the ultraviolet light from pixel array 220. The observer absence detector may include a camera on a touchscreen cell phone that visually determines the absence of observers. In one example the absence detector may simply detect that observers have their eyes closed or are a certain minimum distance away. In another example, the absence detector may be a motion detector or infrared detector detecting any movement or body in the vicinity of the device. In another example the absence detector detects if the device is being held in the hand of a user by a capacitance or other detector, then the absence detector may detect that it is not being held. In another example the observer absence detector determines if the observer has a line-of-sight view of the ultraviolet light or is otherwise able to view the ultraviolet light. The description is not limited to any particular form of observer absence detection and many observer absence detection techniques are known to those familiar with the art. Other examples of observer absence detection include user proximity detection and determining if the cell phone is holstered or if the touchscreen is placed face down on a surface, or otherwise covered by a display cover or in the case of a flip phone, laptop, or other hinged device, the display may be covered when the device is folded closed.

Atmospheric sensor 252 senses the atmospheric conditions in the vicinity of the device and provides an atmospheric condition signal. The atmospheric sensor may include a thermometer for sensing ambient temperature, a barometer for sensing ambient pressure, and a hydrometer for sensing ambient humidity. These sensors are useful in determining the pathogen environment about the device. In other example implementations, the sensors need not be incorporated within the device 110 and may remotely communicate atmospheric information to the device. In one example, the atmospheric condition signal may be obtained from weather information available from a weather information source 262 on the Internet. Knowing the pathogen environment is useful in adapting pathogen sterilization techniques. For example, if the atmospheric condition signal indicated an environment more conducive to pathogens, then a more aggressive sterilization approach may be implemented.

Operator health sensor 254 determines the operator health condition and generates an operator health condition signal. The operator heath sensor may include a thermometer or infrared sensor for determining the temperature of the operator. A pulse monitor may determine the operator's heart rate. A perspiration monitor may be incorporated in the phone to test the operator perspiration further helping in determine the operator health condition. Also a communications monitor may analyze information and communications to and from the operator to for descriptions of an operator's health. For example, the operator may send a text including the phrase "I feel sick today" which is indicative of a reduced health condition. In another example, the operator may have used the device to purchase cough medication using an NFC or other transaction, indicating the likelihood of a reduced health condition. The communications monitor may be operated remotely from device as a cloud services process 264 analyzing operator related communications for information, such as emails, texts, instant messages, social media exchanges, and other transactions that relate to the health of the operator. Knowing the operator health condition is useful in adapting pathogen sterilization techniques. For example, if the operator health condition signal indicated the operator's health has been weakened, then more aggressive sterilization approaches may be implemented.

The device also includes a modem 256 including a receiver and a transmitter providing access to remote information on the Internet 258 or cloud services or public health information 260. The modem may be any wired or wireless modem, including an Ethernet modem, a cellular modem, a Wi-Fi modem, and/or a Bluetooth modem. Public health information 260 provides a public health condition signal indicative of the public health condition and may be implemented by a cloud bases service generating the public health condition signal. The cloud bases service may use the location of the device in determining the public health condition signal. The cloud based service may interface with health monitoring organizations such as the Center for Disease Control (CDC) or various hospitals or other organizations that release information regarding known or forecasted outbreaks of one or more diseases. Also, the cloud base service may determine seasonal variations in pathogens in generation of the public health condition signal. Knowing the public health condition is useful in adapting pathogen sterilization techniques. For example, if the public health condition signal indicated a currently known outbreak of a disease existed in the vicinity of the device, then more aggressive sterilization approaches may be implemented.

The device also includes a finger input accumulator 270 for accumulating finger inputs and corresponding finger input locations and a stylus input accumulator 272 for accumulating stylus inputs and corresponding stylus input locations. These accumulators also accumulate the duration a location receives a respective input. The finger input accumulator may be initialized after the touch input is sterilized. The initialized accumulator may have zero values or other determined value.

A user interface reorganizing module 274 analyzes the accumulated touch inputs and corresponding touch locations and determines, based on the analyzing, lesser touched locations on the touchscreen. The lesser touched locations are indicative of locations on the touch screen having less potential for pathogens. Then the user interface is reorganized based on the lesser touched locations in an effort to reduce the likelihood of the transfer of pathogens between users of the touch input device. In one example, the user interface reorganizer locates a user interface icon at a lesser touched location. User interface reorganization has advantages in applications such as touchscreen kiosks where a number of operators may access the touch surface with a number of touch inputs before the touch surface can be sterilized. Furthermore repetitive touches of a touch surface by a stylus 245, may do little to spread pathogens, but may increase the wear and tear on the touch surface receiving touch inputs from both fingers and styluses. User interface icons may further be reorganized to lesser stylus touched locations on the touchscreen to reduce stylus wear and tear on specific areas of the touchscreen. Reduction of wear and tear on a touchscreen by objects like a stylus results in a "touchscreen saver" that extends the operational life of the touchscreen while further providing for pathogen transmission mitigation. In this example, sterilization of the touchscreen may result in the initializing of the finger input accumulator 270, because pathogens on the touch surface have been sterilized, but not the stylus input accumulator 272, because stylus wear and tear of the touch surface continues.

Controller 280 includes a processor for controlling the functions of the device. The controller 280 may include a microprocessor, a computer, a reduced instruction set computer, an application specific circuit, and a custom integrated circuit. It may include an operating system and applications which are used for render user interface icons on the display 230 and receiving touch inputs on the touch input surface 210. The controller may include or access an ultraviolet pixel selector and modulation module 282. Module 282 selects pixels and modulates the ultraviolet illumination luminosity and duration of the selected pixels. Module 282 acts as a risk management module in that ultraviolet light is modulated to provide sufficient illumination to sterilize the touch surface while minimizing unnecessary exposure to observers and avoiding excessive power consumption. The controller also accesses a computer program product stored in program memory 284 for implementing methods performed by the device. Program memory includes RAM, ROM, removable media and other forms of memory storing computer code or executable computer instructions. Program memory 284 represents a storage medium readable by a processing circuit such as controller 280, that when executed by the processing circuit performs the methods described herein. The program media represents a nontransitory computer readable medium having a stored set of instructions that when executed cause an device to implement the methods described here.

Figure 3:
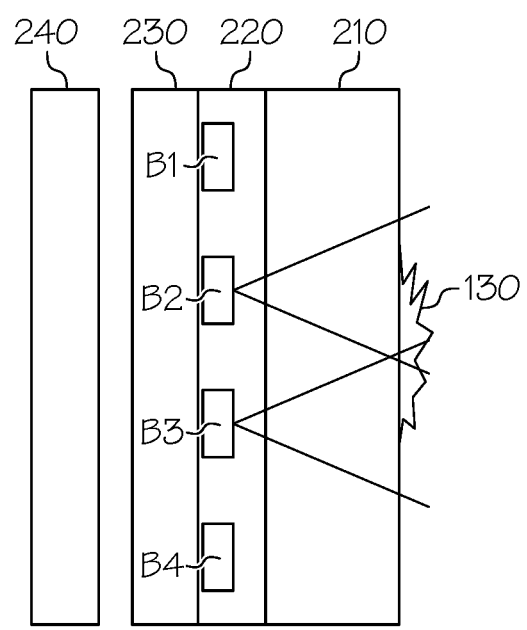
FIG. 3 illustrates an example of a cross section of a touch input device with pathogen transmission mitigation using selective touch area sterilization.

FIG. 3 illustrates an example of a cross section of a touch input device with pathogen transmission mitigation using selective touch area sterilization. The cross section of FIG. 3 represents a portion of the touch input surface 120 around touch location 130. Four pixels of the array are shown as B1, B2, B3 and B4. Pixels B2 and B3 are shown illuminating touch location 130 thereby sterilizing pathogens associated with the touch input of FIG. 1. Based upon the example ultraviolet calculations above, sterilization pixels B2 and B3 radiate ultraviolet light with a wavelength of 264 nm, with an illumination luminosity and duration intended to sterilize the selection portion of the touch surface. As will be discussed in more detail below, the ultraviolet luminosity and duration can be modulated based upon several factors depending on the aggressiveness of the sterilization. Pixels B1 and B4 are shown as OFF, thereby conserving power and limiting unnecessary radiation of ultraviolet light. FIG. 3 shows the pixel array radiating the from the rear of the touch input, in another example, the pixel array may be located around one or more edges of the touch surface 210, thereby providing ultraviolet light from the sides of the touch surface.

Figure 4:
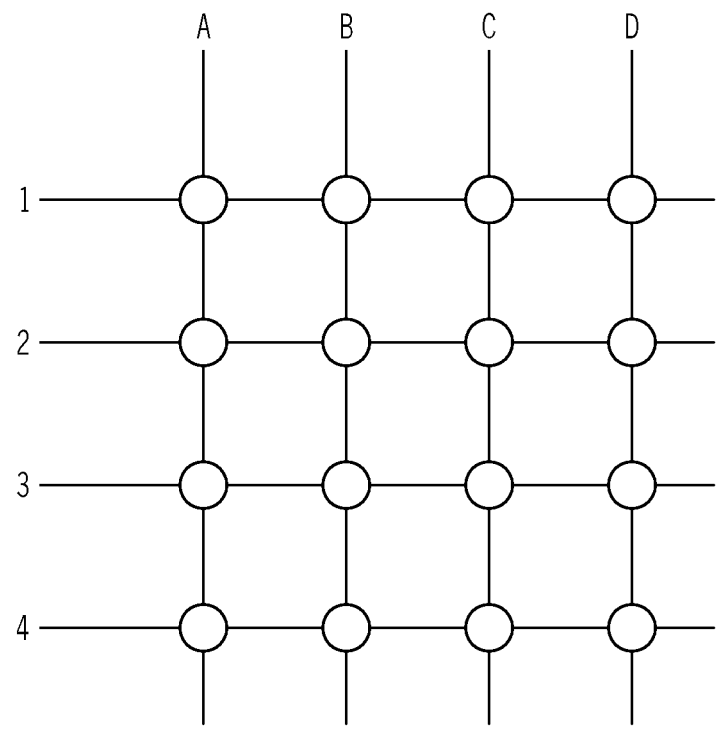
FIG. 4 illustrates an example of a portion of an ultraviolet pixel array.

FIG. 4 illustrates an example of a portion of an ultraviolet pixel array. Sixteen pixels are shown, each pixel comprising a GaN based diode. The array comprises four columns, A, B, C, D and four rows 1, 2, 3, 4. Single and multiple pixels may be selected for illumination using row/column pixel strobing or multiplexing techniques known to those familiar with the art. For example providing a ground charge on column B while providing positive voltages on rows 2 and 3 and floating rows A, C and D will selectively illuminate only pixels B2 and B3 of the pixel array. The illumination luminosity and duration can be modulated during illumination. Illumination luminosity may be modulated by varying the level of positive voltage or current and the illumination duration may be modulated based upon the length of time that the voltage is present. For example, doubling the current provided to a pixel may result in a doubling of the luminosity, or the rate of ultraviolet photons per second illuminating the portion of the touch surface. Doubling the duration results in a doubling of ultraviolet photons illuminating the selected portion of the touch surface given a constant luminosity. The pixel density of the pixel array used in a device may be varied while remaining within the scope of this description. In one example the pixel density is 16 pixels per square centimeter or 4 pixels per centimeter.

Figure 5:
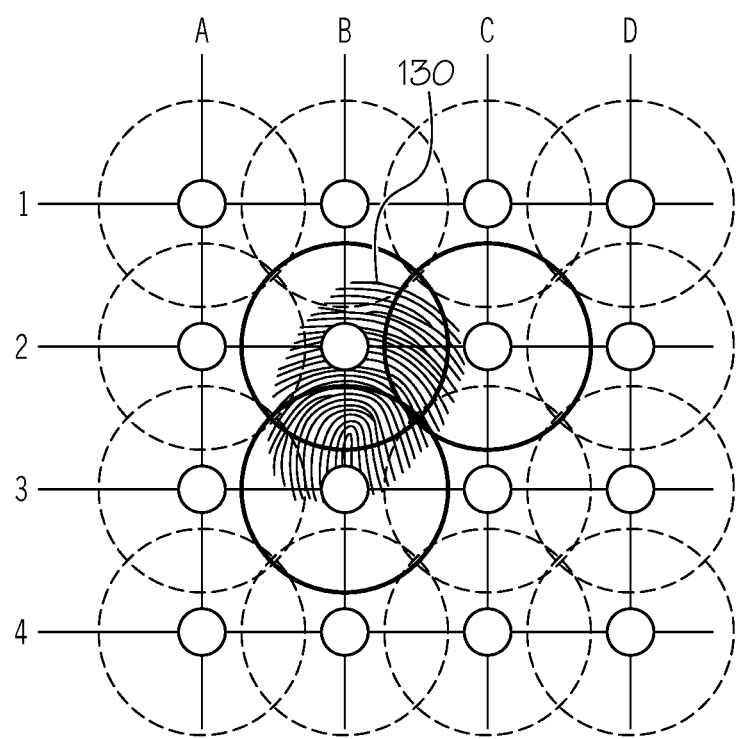
FIG. 5 illustrates an example of a pixel array illuminating a portion of a touch surface having pathogens where each pixel of the array is configured to illuminate a portion of the touch surface with an ultraviolet light of a sterilization wavelength.

FIG. 5 illustrates an example of a pixel array illuminating a portion of a touch surface having pathogens where each pixel of the array is configured to illuminate a portion of the touch surface with an ultraviolet light of a sterilization wavelength. As in FIG. 4, a portion of a pixel array comprises four columns, A, B, C, D and four rows 1, 2, 3, 4, wherein each pixel is shown as a small circle at an intersection of a row and a column. Each pixel illuminates a corresponding portion of the touch surface as shown by larger circles centered at each row column intersection. Also shown is touch location 130. Touch location 130 may be sterilized by selecting and illuminating pixels B2, B3, and C2. These three portions of the touch surface illuminated by pixels B2, B3 and C2 are shown as solid lined circles while the other portions of the touch surface potentially illuminated by other pixels in the array are shown by dashed lined circles. As a synergistic benefit shown in FIG. 5, a touch input has a dual purpose of receiving a touch input at a touch location to control a computer operated device application and also to provide touch location information to selectively illuminate a portion of the touch surface based on the touch input.

In one example of FIG. 5 there is one touch location 130 on the touch surface which is selectively sterilized by illuminating pixels B2, B3 and C2. In other examples, additional pixels may be illuminated to provide a more aggressive sterilization. Such additional pixels include A2, A3, B1, C1 and C4, because they also illuminate a portion of the touch surface including the touch area.

In one example, more than one UV emitter may be used to illuminate touched locations. The best combination of UV emitters and their sequence of illumination may be selected to minimize total power consumption. One solution to this selection and temporal ordering problem is an optimization, where the set and sequence of regions to illuminate with a combination of sources in order to reach a threshold flux of photons in each region while minimizing overall flux is computed. Note that each of the UV emitters may only cover a portion of touch locations. As second example to accomplish this is to perform random sampling over the array of candidate emitters, and employ a model of their expected flux over a set of regions on the touch screen corresponding to the touched region. By accumulating these expected flux quantities for each region, based on the expected emission profile of each emitter, illumination may proceed until the desired profile is achieved (for example a uniform distribution of fluxes over all regions, exceeding some threshold for sterilization).

Building on the example of FIG. 5, other sterilization approaches can be implemented after several touch inputs have been occurred. In this case the touch locations and corresponding durations are accumulated between sterilizations. Then the corresponding portions for illumination of the display are selected based upon the accumulated touch input locations. The luminosity and the duration of the illumination may be adjusted based upon the accumulated durations. For example, if a first touch location has an accumulated duration of touch inputs twice that of a second location, then both pixels may be illuminated for the same duration while the sterilization luminosity of the portion of the touch input corresponding to the first location may be twice the luminosity of the second portion of the touch input corresponding to the second location. Alternately, both portions may be illuminated with the same luminosity, with the first portion illuminated for twice the duration of the second portion. Thus both portions of the touch surface are sterilized, but the second portion receiving either half the duration or half the luminosity of the first portion. This approach sterilizes both portions but conserves power where less sterilization is determined to be needed.

An approach to a level loaded illumination, from a power consumption perspective, is to determine which portion of the display requires the longest duration of illumination at a desired level of luminosity and modulate the luminosity of other portions of the display selected for illumination to a reduced luminosity to provide a desired amount of ultraviolet radiation. In this way, all pixels selected to be illuminated are illuminated for the same duration with differing levels of luminosity. Another approach to controlling ultraviolet radiation of touch locations is to illuminate all selected pixels with the same luminosity and modulate the duration of illumination of each portion to provide the desired amount of ultraviolet radiation for each portion of the touch surface selected for illumination. Other approaches to modulating illumination luminosity and illumination duration may implement while remaining within the scope of the description. Such approaches have the advantage of conserving power by not illuminating unnecessary portions of the touch input during sterilization, and reducing the power consumed on areas to be sterilized that are determined to have less pathogens, based upon accumulated touch locations and corresponding durations.

After accumulating touch locations and corresponding durations the trigger for selective sterilization of portions of the touch surface may be based upon by any of a number of events including the aforementioned determined absence of observers. It may also be based upon one or more of a manual input such as a gestural trigger indicating a sterilization request from an operator of the device, an accumulated total number of touch inputs, an accumulated total duration of touch inputs, atmospheric conditions, operator health conditions and the public health conditions. For example, if only a single touch input were received since a prior sterilization, and the operator's health condition was good, the public health condition in the vicinity of the device was good and the atmospheric conditions were not conducive to pathogens on the touch surface, then the sterilization process may be deferred until the next determination absence of observers. This approach has the advantage of conserving power by not sterilizing the touch input at every sterilization opportunity.

Alternately if: a long time had elapsed since the last sterilization, there is a local flu outbreak (as determined by the cell phone accessing the cloud for such information), the operator is developing flu like symptoms (as determined by: the operator manually indicating to the cell phone that such conditions exist, or biosensors associated with the cell phone determining the existence of flu like symptoms, of cloud based monitoring social media where the is an indication of operator flu like symptoms), the local atmosphere provides an environment conducive to the survival of pathogens, and the touch surface received touch inputs from a number of different operators since the last sterilization, then selective sterilization may be triggered immediately upon determining the absence of observes potentially able to be exposed to ultraviolet light. Furthermore, based upon any one or more of these conditions, the illumination luminosity and or duration may be modulated to assure adequate or aggressive sterilization of only pathogen likely portions of the touch surface.

The trigger may also be based upon the location of the device. For example, a device located in a hospital may benefit from a more aggressive sterilization profile than a device located in an environment less conducive to pathogens.

Figure 6:
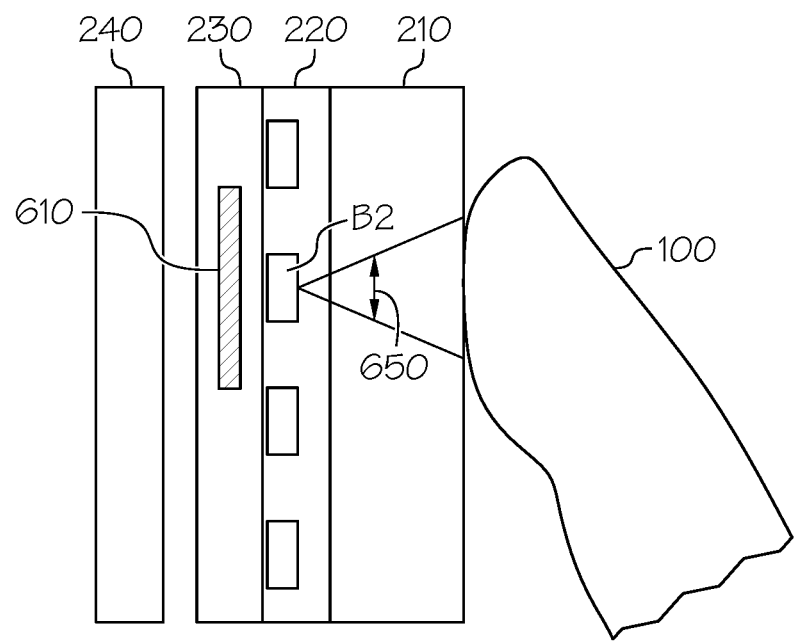
FIG. 6 illustrates an example application of selective illumination of a touch surface where the illuminating occurs during the receiving of a touch input.

FIG. 6 illustrates an example application of selective illumination of a touch surface where the illuminating occurs during the receiving of a touch input. The touch input from the finger 100 of the operator corresponds to the location of user interface icon 610 rendered on display 230. Based on the touch location, the process associated with the user interface icon is implemented by the device. Also based upon the touch location, a portion of the touch surface is selected and illuminated with ultraviolet light 650 of a sterilization wavelength. In this example, pixel B3 of pixel array layer 220 illuminates a portion of the touch surface with ultraviolet light 650, the illuminated portion corresponding to the touch location of the finger 100 of the operator. As the finger of the operator moves across the touch surface, in a swiping gesture for example, other pixels under the finger may be illuminated while illumination of pixels no longer under the finger may be terminated. Furthermore in the event of a multi-touch input, pixels under a plurality of fingers may be illuminated. Ultraviolet illumination during the touch has advantage of not only instantaneously sterilizing the screen only at a selected portion of the screen needing sterilization, but also sterilizing the finger of the operator thereby helping reduce any spreading of pathogens by the operator after using the device. Furthermore, the finger of the operator helps block ultraviolet radiation to eyes of observers of the touchscreen that may otherwise be exposed to the ultraviolet light if not for the finger blocking the ultraviolet light.

The luminosity and duration of the ultraviolet illumination may also be varied in response to a number of factors. For example, the illumination may be limited to a maximum duration or be in the form of a pulse of ultraviolet light at the point of contact of the touch input, or the luminosity may have a decaying level to regulate exposure of a finger to ultraviolet light. In another example, the owner of the device may invoke a different sterilization profile when the handing the device to another "guest" operator, for example the illumination luminosity and duration profile may be set to continuous illumination for guest operators. Furthermore, elements indicative of pathogen levels, such as the local weather, the health of the operator and the local public health conditions, may be taken into account to increase or decrease the exposure of ultraviolet radiation while receiving the touch input.

Also the amount of ultraviolet exposure of an operator may be monitored over time and the illumination varied in response thereto. Another advantage of the system is to avoid undesirable over exposure of the operator to ultraviolet light. The ultraviolet illumination may be modulated to maintain the ultraviolet exposure to an amount below a harmful amount thereby avoiding undesirable overexposure. Further safety systems may be incorporated into the device that further assure the user is not over exposed to harmful amounts of ultraviolet light, thereby assuring that the benefit of ultraviolet radiation exceeds any potential harm, while remaining within the scope of this description. For example, ultraviolet radiation may be terminated in the event of excessive power or temperature fluctuations or even excessive activations of ultraviolet pixels over a period of time while the device is being touched.

Figures 7, 8:
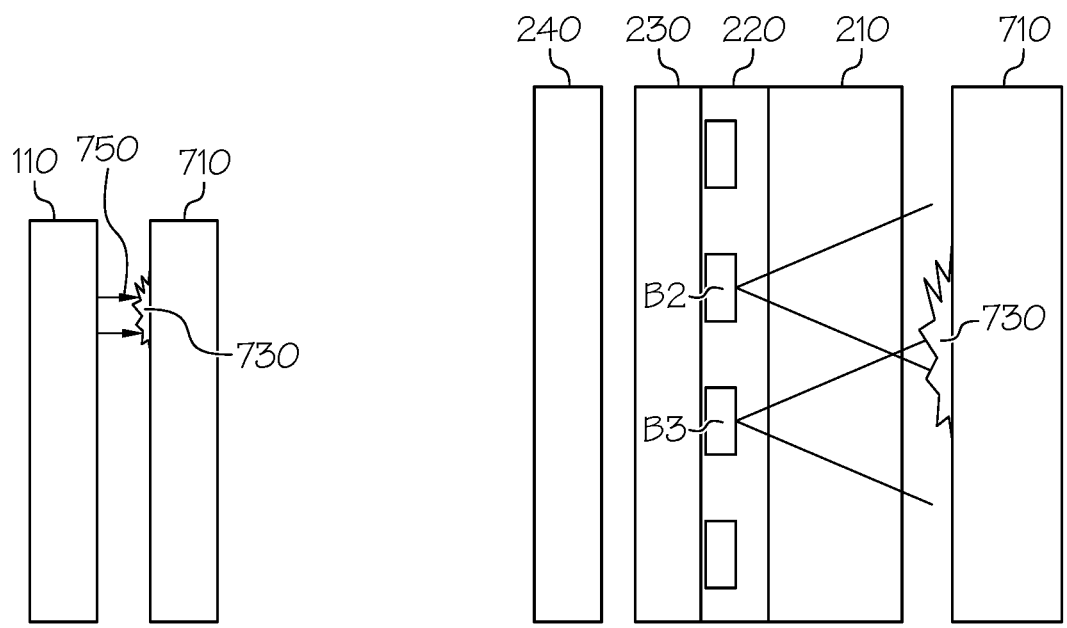
FIG. 7 illustrates an example application of selective illumination of a touch surface of a peer device.
FIG. 8 illustrates a more detailed cross section of the application of FIG. 7.

FIG. 7 illustrates an example application of selective illumination of a touch surface of a peer device. The peer device 710 does not have to be of the same maker as the sterilizing device 110, and the peer device 710 would not have the UV array capability. The sterilizing device 110 and the peer device 710 may have an application that enables the screen alignment of the two devices. Furthermore peer device 710 may supply sterilizing device 110 with the history of touch location on its screen. In this example, a peer device 710 has received a peer touch input on its peer touch surface at peer touch location 730, indicating a portion of the peer touch surface may have pathogens. Peer device 710 can be sterilized by device 110. The devices aligned and an alignment signal is received by device 110. Alignment may be simply placing identical sized devices face to face with tops, bottoms and sides aligned, thereby aligning the touch surface of device 110 with the peer touch surface of peer device 710. Device 110 also receives a peer sterilization signal indicative of the peer touch input received at peer touch location 730 on a peer touch surface. Device 110 then the selects a portion of the peer touch surface based upon the peer touch location and the alignment signal and illuminates the portion of the peer touch surface with ultraviolet light 750, thereby sterilizing pathogens at the portion of the peer touch surface corresponding to the touch input.

The alignment signal may be entered manually at device 110 or determined locally by device 110 or determined by both devices 110 and peer device 710 using any of a number of methods while remaining within the scope of this description. For example, device 110 can detect one or more optical or magnetic fiducial markers on device 710. The image from one or more cameras on the device may be compared with a pre-stored reference image of the peer device. Based on the reference image and the camera image, as user brings the devices together, instructions on moving the device left, right, up or down or rotating the device clockwise or counter clockwise relative to the peer device may be provided in order to assist with alignment. The peer sterilization signal may include one or more touch locations and optional corresponding touch durations and may be communicated using any number of techniques including USB, Bluetooth, Wi-Fi, Zigbee, NFC or other short range, peer-to-peer or device to device communication techniques. The peer sterilization signal may also include peer touch surface dimensions and locations relative to the alignment signal in the event the touch surface dimensions and the peer touch surface dimensions are not identical. Finally in one example, device 110 need not include a touch surface or display and backlight to implement the peer sterilization of FIG. 7. In this example, the device may act as a dedicated portable sterilization device for selectively sterilizing touch input surfaces of multiple kiosks in a mall or other retail setting for example, and thus may be included as part of the nightly janitorial maintenance routines.

FIG. 8 illustrates a more detailed cross section of the application of FIG. 7. Touch location 730 of device 710 is shown to be selectively illuminated by pixels B2 and B3 of pixel array 220 of device 110. Pixels B1 and B4 are off and conserving power and are not required to illuminate the portion of the touch input corresponding to touch location 730.

Figure 9:
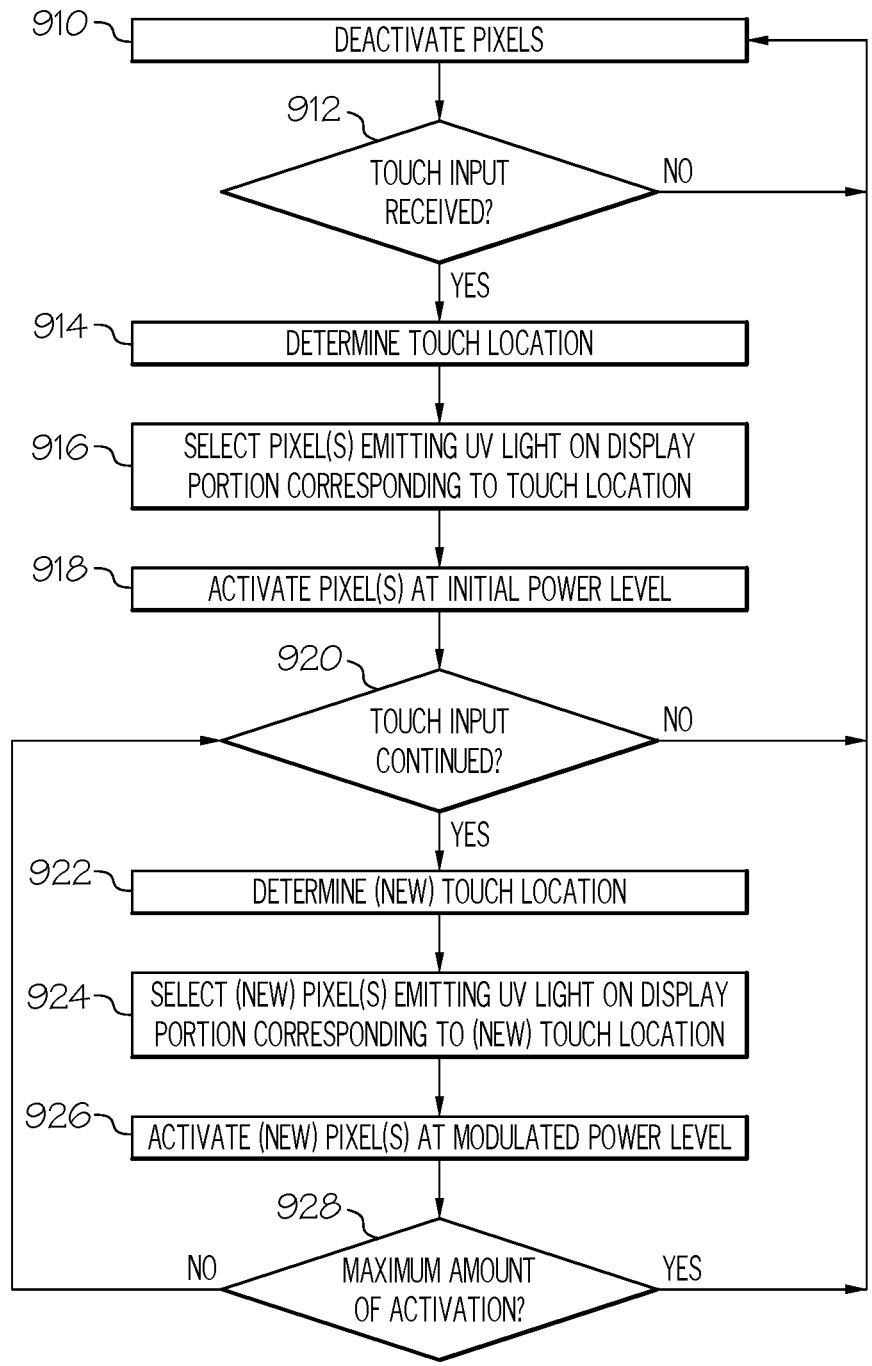
FIG. 9 illustrates an example flow diagram of a process for selective illumination of a touch surface where the illuminating occurs during the receiving of a touch input as shown in FIG. 6.

FIG. 9 illustrates an example flow diagram of a process for selective illumination of a touch surface where the illuminating occurs during the receiving of a touch input as shown in FIG. 6. In step 910 all pixels are deactivated and step 912 determines if a touch input is being received. If so, then step 914 determines a touch location of the touch input and step 916 selects which pixel(s) illuminate a portion of the touch surface corresponding to the touch location. Step 918 then activates the pixels at an initial power level. If at step 920 a touch input is no longer being received, then returning to step 910 deactivates the pixel(s). However, if the touch input continues, then step 922 determines the location of the continuing touch input and step 924 selects which pixel(s) illuminate a portion of the touch surface corresponding to the current touch location. If the current touch location had not changed, then the prior pixels would be selected. Step 926 activates the selected pixel(s) at a modulated power level resulting in a modulated luminosity. In one example, reducing the power level over time reduces the finger's exposure to ultraviolet radiation during the touch input. Step 928 determines if the finger has been exposed to a maximum amount of ultraviolet radiation. If so, step 910 deactivates the pixels and in this example, pixel deactivation may continue for a determined time. If the maximum amount is not been reached at step 928, then step 920 continues to determine if the touch input is continued to be received. Thus, the flow diagram of FIG. 9 shows selectively illuminating a portion of a touch input while the touch input is being received, the illuminated portion corresponding to the location of the touch input. Furthermore, the illumination of the finger providing the touch input is modulated to avoid over exposing the finger to ultraviolet illumination. In the example of FIG. 9, an observer absence detector may not be required because the touch finger may otherwise obscure undesired ultraviolet radiation.

Figure 10:
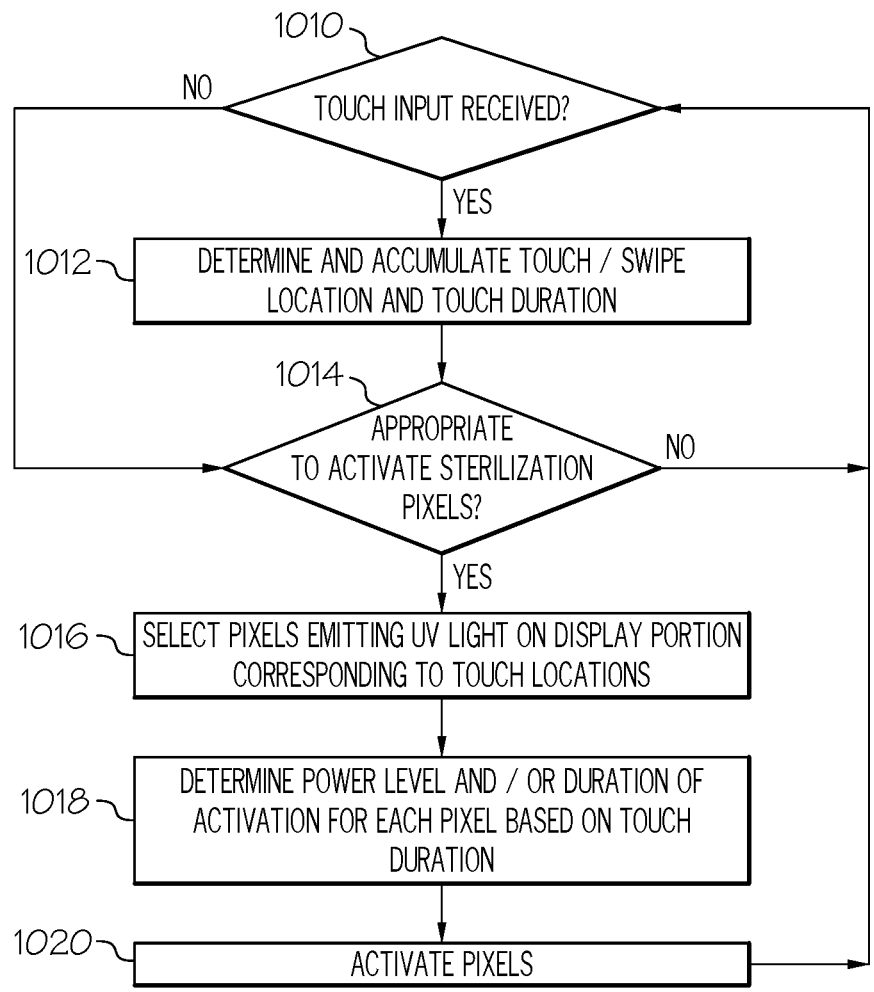
FIG. 10 illustrates an example flow diagram of a pixel array illuminating a touch surface having pathogens where each pixel of the array is configured to illuminate a portion of the touch surface with a modulated luminosity and duration ultraviolet light of a sterilization wavelength as shown in FIG. 5.

FIG. 10 illustrates an example flow diagram of a pixel array illuminating a touch surface having pathogens where each pixel of the array is configured to illuminate a portion of the touch surface with a modulated luminosity and duration ultraviolet light of a sterilization wavelength as shown in FIG. 5. When a touch input is received at step 1010, step 1012 determines the touch location and the corresponding touch location and accumulates the information. This step also makes determinations and accumulations for swipe and multi-touch touch inputs. Then step 1014 determines if it is appropriate to activate pixels for sterilization of the touch input. This determination may be based upon a number of elements including absence of observers, atmospheric conditions, health conditions, and number and duration of touch inputs. If appropriate, then step 1016 selects pixels of the array for emitting ultraviolet light on the portion of the touch input corresponding to the touch locations. Then step 1018 determines the power level for illuminating each pixel, thereby modulating the luminosity of each pixel, and the duration of illumination of each pixel. This allows for each selected portion of the touch surface to be illuminated with a luminosity and a duration that is different from other portions of the touch surface. Step 1020 then activates the pixels for the determined durations and illuminations. The pixels may be deactivated at any time during step 1020 if it is no longer appropriate to activate the pixels. For example, if an observe capable of being undesirably exposed to ultraviolet light is detected, then the pixels may be immediately deactivated. FIG. 10 shows accumulating touch input locations and corresponding durations and then selecting portions of the touch input for illumination and then illuminating the selected portions of the touch input.

Figure 11:
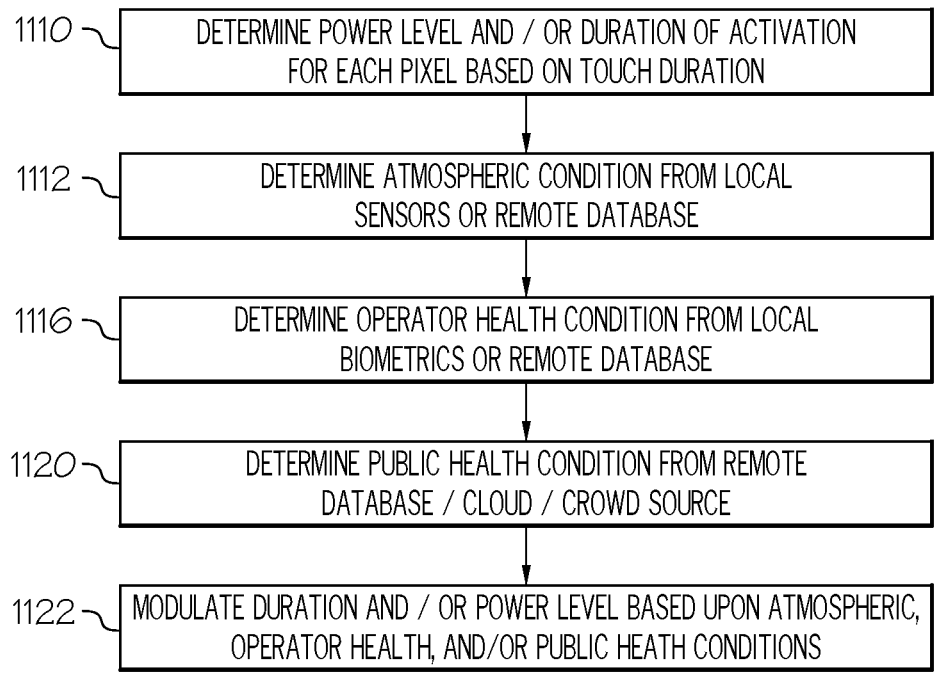
FIG. 11 illustrates an example flow diagram of a process for modulating illumination luminosity and illumination duration based upon the atmospheric condition signal, operator health and public health conditions.

FIG. 11 illustrates an example flow diagram of a process for modulating illumination luminosity and illumination duration based upon the atmospheric condition signal, operator health and public health conditions. FIG. 11 corresponds to a more detailed implementation of step 1018 of FIG. 10. Step 1110 determines the power level or luminosity of illumination and/or duration of activation for each selected pixel based upon accumulated touch duration. In an example of a swipe gesture, the swipe gesture may result in receiving the touch input at a first of the plurality of touch locations for a first duration and a second of the plurality of touch locations for a second duration. The process of selecting pixels for illumination selects a first portion of the touch surface for illumination based upon the first touch location of the swipe gesture and selects a second portion based upon the second touch location of the swipe gesture. The illuminating process modulates luminosity and/or duration of the first portion of the touch surface based upon the first duration, and modulates luminosity and/or duration of the second of the plurality of portions based upon the second duration. Thus if a swipe gesture resulted in a touch input being received in a first location for a duration twice that of a second location, the illumination luminosity or duration of the first portion of the touch surface corresponding to the first location could be twice that of the second portion corresponding to the second location.

Step 1112 determines the atmospheric condition from either a local sensor such as atmospheric sensor 252, or from a remote database, such as weather service 262. If the atmospheric condition is less conducive to pathogens, then power can be conserved by reducing the luminosity of duration of illumination of selected pixels. Step 1116 determines the operator health condition from either a local sensor such as operator health sensor 254, or from a remote database, such as operator health service 264. If the operator health condition is less conducive pathogen spreading, then power can be conserved by reducing the luminosity of duration of illumination of selected pixels. Step 1120 determines the public health condition from a remote database, such as public health service 260. If the public health condition is less conducive pathogen spreading, then power can be conserved by reducing the luminosity of duration of illumination of selected pixels. Step 1122 modulates the duration and/or power level (thereby modulating the luminosity) of each selected pixel based upon the atmospheric, operator health, and/or public health condition. In other examples, only one or two of the three conditions of FIG. 11 can be used in modulation luminosity and duration of a sterilizing illumination.

Figure 12:
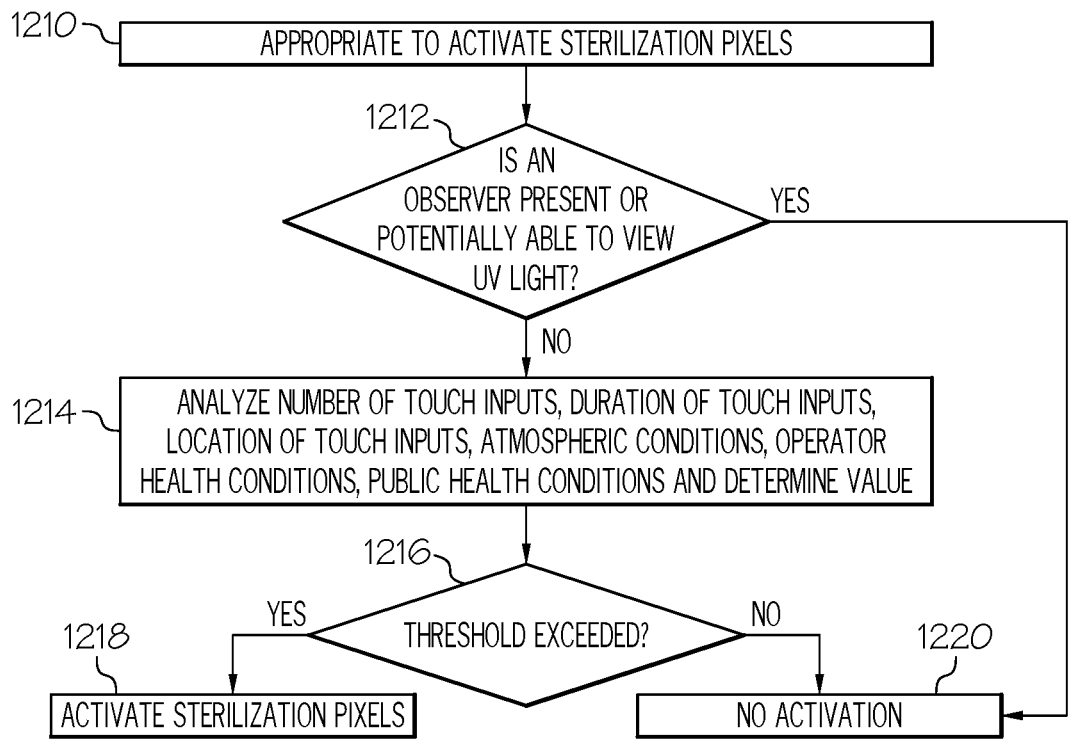
FIG. 12 illustrates an example flow diagram for determining the appropriate conditions for activation of sterilizing pixels.

FIG. 12 illustrates an example flow diagram for determining the appropriate conditions for triggering activation of sterilizing pixels. FIG. 12 corresponds to a more detailed description of step 1014 of FIG. 10. The flow diagram enters at step 1210 and step 1212 determines if an observer is present or potentially able to be exposed to ultraviolet light from the device. As previously described, this determination may be made in a number of ways while remaining within the scope of the description including monitoring information from observer absence detector 250. If an observer is not absent, then no activation is indicated at step 1220. If no observer is detected, then step 1214 determines an aggressiveness of the appropriateness of pixel activation. The aggressiveness may be based upon analysis of one or more factors for determining opportunities for pathogens to be transferred to the touch surface including the accumulated number of touch inputs and/or the accumulated duration of touch inputs and/or the location of the touch inputs since the last sterilization. The aggressiveness may also be based upon the potential amount of pathogens transferred with each touch input and surviving on the touch surface including the atmospheric conditions, the operator health and the public health conditions. Upon exceeding a threshold at step 1216, then the flow diagrams exits at step 1218 indicating that it is appropriate to active sterilization pixels. A number of different formulas may be used to determine the appropriateness of pixel activation based upon the factors described herein. For example, the threshold may be exceeded after six touch inputs of one second each are accumulated under nominal weather and health conditions. However, if the operator's health condition were determined to be reduced, then the threshold may be exceeded after three touch inputs of one second each. Furthermore, activation of ultraviolet pixels may be terminated or the illumination otherwise attenuated at any time if it is determined that an observer in the vicinity of the device may be undesirably exposed to ultraviolet radiation.

Figure 13:
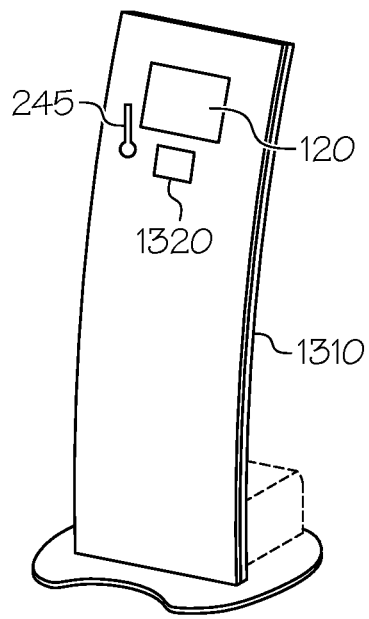
FIG. 13 illustrated an example of a touch input device with pathogen transmission mitigation by user input reorganization.

FIG. 13 illustrated an example of a touch input device with pathogen transmission mitigation by user input reorganization. Device 1310 is shown as a kiosk which may be located in a public place and operated by many different operators. Kiosks may be used for multiple purposes known to those familiar with the art including advertising, information and directions and facilitating financial and credit card transactions and purchases at a point of sale. The kiosk has a display 120 which may or may include a touchscreen. The kiosk also has a touchpad 1320 which may, in for example, complement a display which does not have a touch input surface. The kiosk also has a stylus 245 which may be used with either or both the display 120 and the touchpad 1320. Display 120 and touchpad 1320 may receive touch inputs for either or both the stylus and the finger of the operator. While a kiosk 1310 is illustrated for purposes of example, the advantages of user interface reorganization for pathogen mitigation, as described herein, may be realized by any device receiving touch inputs while remaining within the scope of this description.

Figure 14:
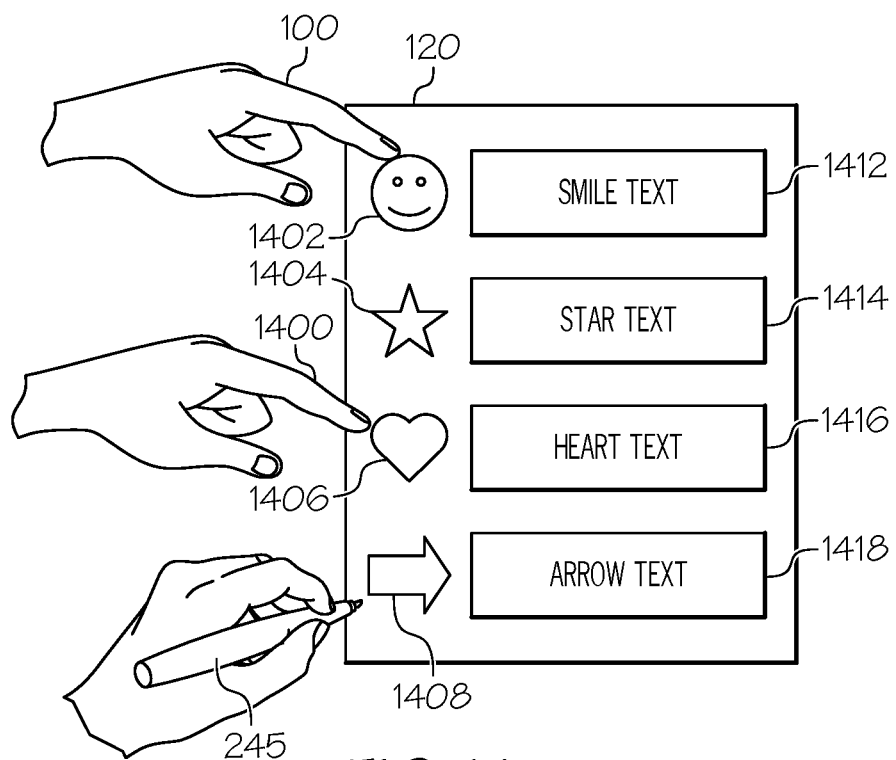
FIG. 14 illustrates an example of a user interface screen rendered on a touchscreen having been touched by a stylus and fingers.

FIG. 14 illustrates an example of a user interface screen rendered on a touchscreen having been touched by a stylus and fingers. Rendered on touchscreen 120 is one screen of a user interface which includes four user interface icons 1402, 1404, 1406, and 1408 and four corresponding information fields 1412, 1414, 1416, and 1418 associated with the user icons. While user interface icons are described in this example are images, within the scope of the description user interface icons mean any rendered image, which when touched result in a computer response, such as hypertext links and other image objects with embedded URLs or other computer instructions. The information fields are descriptive to the operator and when touched do not necessarily cause specific actions by the computer. Information fields may be descriptive text, may be "white space" or may contain any other information for aiding the operator. A user interface may include a number of screens, each screen may be a rendering associated with an operating system, an application, a web page or any other screen rendered by the device. Icon 1402 is shown as having been touched by operator finger 100, icon 1406 is shown as having been touched by operator finger 1400 and icon 1408 is shown as having been touched by stylus 245. Consequently, pathogens may have been transferred to the touch surface at icons 1402 and 1406, but not at icon 1404 because it was not touched, and also not at icon 1408 because it was touched by the stylus which is less likely to transfer pathogens. Assuming the touch surface was sterilized prior to the touches shown in FIG. 14, future finger touches of icons 1402 and 1406 may result in the transfer of pathogens and thus the spread of disease. However, other areas of the touch surface have not been touched by fingers and are presumably sterile. Thus, touches at these other areas will not likely result in the transfer of pathogens thereby avoid the spread of disease.

Figures 15, 16:
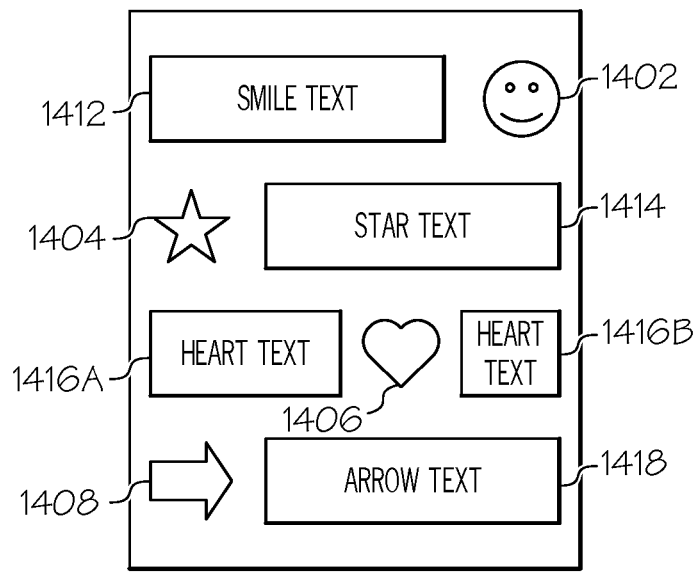
FIG. 15 illustrates an example of the user interface screen of FIG. 14 after a reorganization based upon stylus and finger touches.
FIG. 16 illustrates an example of data held in touch input and stylus input accumulators.

FIG. 15 illustrates an example of the user interface screen of FIG. 14 after a reorganization based upon stylus and finger touches. In order to mitigate the transfer of pathogens, the touch inputs of FIG. 14 were accumulated and analyzed and the screen of FIG. 15 has reorganized icons to lesser touched locations on the touch surface. Icons 1402 and 1406 were touched by fingers and moved to lesser touched locations, the lesser touch locations corresponding to former rendered locations of information fields 1412 and 1416. Information fields 1412 and 1416 were also reorganized for rendering at locations on the touch screen which were previously touch by fingers. Icons 1404 and 1408 and information fields 1414 and 1418 were not touched by fingers and their locations were not reorganized in FIG. 15. Relocating icons 1402 and 1406 to lesser touch locations on the touchscreen reduces the likelihood that a future touch of the icons will result in the transfer of pathogens that may have been transferred to the touch surface by the touches of FIG. 14, thereby mitigating transmission of pathogens.

FIG. 16 illustrates an example of data held in touch input and stylus input accumulators. The finger input accumulator 270 and the stylus input accumulator 272 are shown in FIG. 2. The data of FIG. 16 is arranged in a matrix. In this example, each cell corresponds to a location on a touch surface. Shown are sixteen cells in four columns, A, B, C, D and four rows 1, 2, 3, 4. Each cell includes two pairs of entries, the upper pair of entries corresponds to touch inputs and the lower pair corresponds to stylus inputs. The first entry of a pair corresponds to an accumulation of a count touch inputs received at the location and the second entry of the pair corresponds to an accumulation of the total duration that touch inputs have been received at the location. For example, cell A1 has received 65 touch inputs for a total duration of 92 seconds and 240 stylus inputs for a total of 121 seconds. In one analysis example, the touch input accumulation is representative of potential pathogens on the touchscreen and the stylus input accumulation is representative of potential wear and tear on the touchscreen. Upon sterilization, the touch input accumulation may be initialized to a preset value, reset, cleared or initialized to a determined value. For example, the determined value of the initialized finger input accumulator may be calculated by dividing the finger input accumulator values by ten after sterilization, or by twenty after an aggressive sterilization. In another example, since the growth of bacteria is time dependent, the time of the touch may be stored and the luminosity and duration of illumination modulated based on the elapsed time determined from the time of the touch.

Reorganizing a user interface screen includes accumulating touch inputs and corresponding touch locations received on a touch screen, analyzing the accumulation to determine an at least one lesser touched location on the touchscreen, and rendering a user interface icon at a location on the touchscreen based upon the receiving. FIG. 16 shows an example of an accumulation of touch inputs and corresponding touch locations. In another example, the accumulation may include significantly more data on significantly more locations. Analyzing the accumulation of FIG. 16 to determine lesser touched locations may be performed in a number of different ways while remaining within the scope of the description. If, for example, the matrix of FIG. 16 were to correspond to locations on touchscreen 120 of FIG. 14, then icons 1402, 1404, 1406 and 1408 would have touch input locations corresponding to cells A1, A2, A3, and A4 of FIG. 16. Further, information fields 1412, 1414, 1416, and 1418 would have touch input locations corresponding to cells B1-D1, B2-D2, B3-D3, and B4-D4, respectively.

Analyzing row 1, cell A1 has the highest finger touch inputs with 65 touch inputs and a 92 second duration. Cells B1, C1 and D1 have equal finger touch accumulations with three touch inputs for two seconds of duration and are thus analyzed to be the lesser touched locations in row 1 of the touchscreen. Thus the analysis indicates that if icon 1402 is to be maintained in row 1, then the icon could be reorganized into locations corresponding to either of cells B1, C1, or D1 in order to mitigate transmissions of pathogens. However, further analysis of the stylus input accumulation indicates that cell D1 has the lowest number of stylus inputs with 22 inputs at a 4 second duration, and thereby indicating less wear and tear. Thus, in order to mitigate wear and tear on the touch screen, analysis further indicates that locating icon 1402 at D1 is a lesser touched location when analyzing both finger inputs and stylus input accumulations. FIG. 15 shows icon 1402 being rendered at location corresponding to D1 on the touch screen based on the analysis.

Analyzing row 3, cell A3 has the highest finger touch inputs with 125 touch inputs and a 321 second duration. Cell C3 has the fewest number to finger touch inputs for the shortest accumulated duration and cell C3 is thus analyzed to be the lesser touched locations in row 3 of the touchscreen. Thus the analysis indicates that if icon 1406 is to be maintained in row 3, then it could be reorganized into a location corresponding to cell C3 in order to mitigate transmissions of pathogens. Further analysis of the stylus input accumulation indicates that all cells in row 3 have the equal stylus input accumulations and mitigating wear and tear of the touch screen has little bearing on the analysis. Thus, locating icon 1406 at C3 is a lesser touched location when analyzing both finger inputs and stylus input accumulations. FIG. 15 shows icon 1406 being rendered at location corresponding to C3 on the touch screen based on the analysis.

The data of FIG. 16 can also be used by a pathogen illustrating application to show pathogen areas of the touchscreen to an observer of the touchscreen. For example, high pathogen areas with accumulated finger touch durations greater than 90 seconds can be rendered in red, low pathogen areas with accumulated finger touch durations less than five seconds can be rendered in green and medium pathogen areas with touch durations between high and low can be rendered in yellow. Using the example data of FIG. 16, areas corresponding to cells A1 and A3 would be rendered in red, areas corresponding to cells B3 and D3 would be rendered in yellow and the remaining cells would be rendered in green. The pathogen display application mode may be useful in facilitating the manual sterilization of the touchscreen, or for other informative purposes. Other thresholds and illustration schemes may be implemented for the pathogen display application mode while remaining within the scope of the description.

Figure 17:
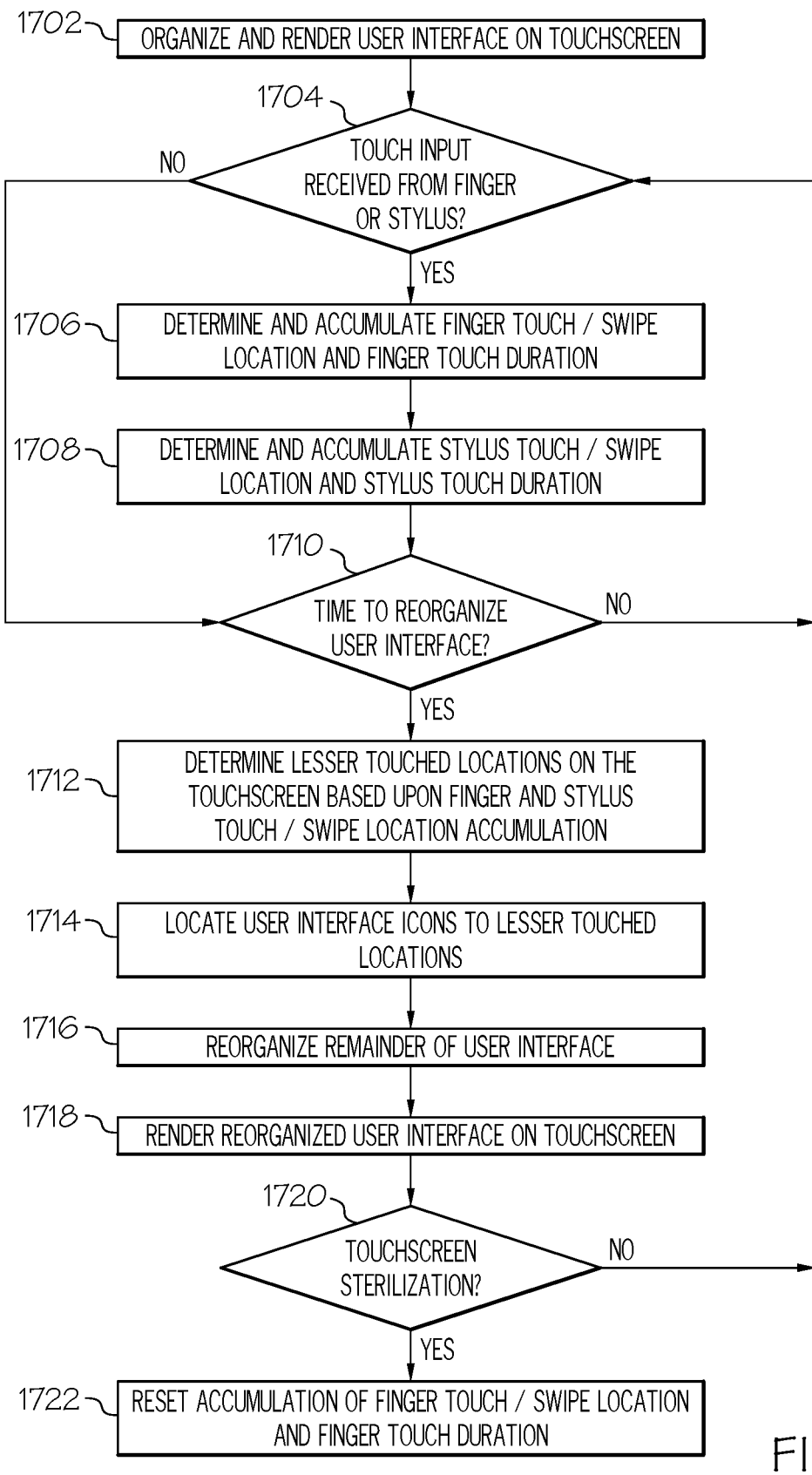
FIG. 17 illustrates a representative flow diagram for reorganizing a touchscreen user interface for mitigating pathogen transmission.

FIG. 17 illustrates a representative flow diagram for reorganizing a touchscreen user interface for mitigating pathogen transmission. Step 1702 organizes a user interface and renders the user interface on the touchscreen. This step could correspond to the organizing and rendering of the screen of FIG. 14. Step 1704 determines if a touch input has been received. If so, step 1706 determines and accumulates finger touch inputs and swipe inputs, their locations and corresponding durations. Step 1708 determines and accumulates stylus touch inputs and swipe inputs, their locations and corresponding durations. Step 1710 determines if it is time to reorganize the user interface. Determining a time to reorganize may be based upon factors described with respect to FIG. 12, except that the absence of observers need not be determined because the illuminating the touchscreen with ultraviolet light in not required as part of the user interface reorganization. On the other hand, the reorganization may not occur until after a current user has completed using the device to avoid any confusion that may result from user interface reorganization while the interface is being used by the current user. Thus, the determination to reorganize the user interface may be based upon a number of factors including the accumulation of finger inputs, an atmospheric condition, an operator health condition, and/or a public health condition. Step 1712 determines lesser touch locations on the touchscreen based upon finger and stylus inputs. Then, user interface icons are located to lesser touched locations at step 1714 and the remainder of the user interface is reorganized at step 1716. Referring to FIG. 14, FIG. 15 and FIG. 16, step 1714 corresponds to reorganizing icon 1402 from location A1 to location D1 and reorganizing icon 1406 from location A3 to location C3, and step 1716 corresponds to reorganizing information field 1412 from cells B1-D1 to cells A1-C1, and reorganization field 1416 from cells B3-D3 to cells A3, B3 and D3. It should be appreciated that the user interface screens of FIG. 14 and FIG. 15 may represent one screen of a user interface having a plurality of screens, a touch input on one screen can result in the rendering of another screen of the user interface, and that reorganization of a user interface can include reorganization of the plurality of screens. The reorganized user interface screen is then rendered on the touchscreen at step 1718. Step 1720 then determines if it is time for touchscreen sterilization. Touchscreen sterilization may be done manually by wiping the screen with a pathogen sterilization chemical or by manually or automatically triggering an ultraviolet sterilization. When wiping the screen with a pathogen sterilization chemical the touch screen can display a color map of the pathogen locations to guide the user cleaning. FIG. 12 shows an example of a process for determining if it is time to sterilize at touchscreen and includes determining if the ultraviolet light is visible by an observer. If ultraviolet sterilization is to be used, the ultraviolet sterilization may selectively sterilize the screen as described herein, or may non-selectively illuminate the touchscreen, bathing it in ultraviolet light. Non-selective illumination may be an effective use of power if the reorganization of the user interface results in a regular distribution of pathogens across the touchscreen area. Upon sterilization, step 1722 resets, clears or otherwise initializes the finger input accumulation but maintains the stylus input accumulation as previously described.

FIG. 14-FIG. 17 also show a method wherein the analyzing determines a plurality of lesser touched locations on the touchscreen, D1 and C3. FIG. 14 shows that the user interface has a plurality of user interface icons 1402-1408, rendered at first locations A1-A4 on the touchscreen and a plurality of information fields 1412-1418 for rendering at second locations B1-D1, B2-D2, C3-D3, D4-D4 on the touchscreen. The user interface is then reorganized based upon the analyzing and rendered on the touchscreen, with icons 1402 and 1406 reorganized from first locations A1 and A3 to second locations D1 and C3. Further note that portions of the information fields have been reorganized into first locations A1 and A3 once occupied by icons 1402 and 1406.

The respective implementations of the present disclosure can be carried out in any appropriate mode, including hardware, software, firmware or combination thereof. Alternatively, it is possible to at least partially carry out the implementation of the present disclosure as computer software executed on one or more data processors and/or a digital signal processor. The components and modules of the implementation of the present disclosure can be implemented physically, functionally and logically in any suitable manner. Indeed, the function can be realized in a single member or in a plurality of members, or as a part of other functional members. Thus, it is possible to implement the implementation of the present disclosure in a single member or distribute it physically and functionally between different members and a processor.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described herein with reference to flowchart illustrations flow diagrams and/or block diagrams of methods, apparatus (systems) and computer program products according to implementations of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the computer or other programmable data processing apparatus, create means for implementing the functions/acts specified in the blocks of the flowchart illustrations and/or block diagrams.

These computer program instructions may also be stored in a computer readable medium that can direct a computer or other programmable data processing apparatus to function in a particular manner, such that the instructions stored in the computer readable medium produce an article of manufacture including instruction means which implement the functions/acts specified in the blocks of the flowchart illustrations and/or block diagrams.

The computer program instructions may also be loaded onto a computer or other programmable data processing apparatus to cause a series of operational steps to be performed on the computer or other programmable data processing apparatus to produce a computer implemented process such that the instructions which execute on the computer or other programmable apparatus provide processes for implementing the functions/acts specified in the blocks of the flowchart illustrations and/or block diagrams.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The present disclosure is described by use of detailed illustration of the implementations of the present disclosure, and these implementations are provided as examples and do not intend to limit the scope of the present disclosure. Although these implementations are described in the present disclosure, modifications and variations on these implementations will be apparent to those of ordinary skill in the art. Therefore, the above illustration of the exemplary implementations does not confine or restrict the present disclosure. Other changes, substitutions and modifications are also possible, without departing from the scope of the description and the appended claims.

What is claimed is:

1. A method comprising:
    determining, with a controller, that a touch input has been received at a touch location on a touch surface;
    selecting, with the controller and based upon the touch location, a portion of the touch surface for illumination with ultraviolet light of a sterilization wavelength from at least one pixel of an ultraviolet pixel array comprising a plurality of pixels that are individually selectable by the controller, the selected portion being selected to include the touch location;
    selecting to activate the at least one pixel which is less than the plurality of pixels, and to deactivate the remaining pixels in the plurality of pixels conserving power of a device, to thereby generate with the activated at least one pixel ultraviolet light of a sterilization wavelength to illuminate the selected portion of the touch surface; and
    illuminating, by the activated at least one pixel of the ultraviolet pixel array where each pixel of the array is configured to illuminate a portion of the touch surface, the selected portion of the touch surface with an ultraviolet light of a sterilization wavelength.

2. The method according to claim 1 wherein:
    the determining that a touch input has been received includes determining that the touch input has been received as a swipe gesture in a plurality of touch locations on the touch surface;
    the selecting of a portion of the touch surface selects, based upon the plurality of touch locations, a plurality of portions of the touch surface that includes the plurality of touch locations; and
    the illuminating illuminates the selected plurality of portions of the touch surface.

3. The method according to claim 2 wherein:
    the swipe gesture results in receiving the touch input at a first touch location of the plurality of touch locations for a first touch duration and at a second touch location of the plurality of touch locations for a second touch duration;
    the selecting of a portion of the touch surface selects, based upon the first touch location and the second touch location, a first portion of the touch surface for illumination based upon the first touch location of the swipe gesture and selects a second portion of the touch surface for illumination based upon the second touch location of the swipe gesture; and
    the illuminating modulates luminosity and/or duration of illumination of the first portion of the touch surface based upon the first touch duration, and modulates luminosity and/or duration of the second portion of the touch surface based upon the second touch duration.

4. The method according to claim 3 wherein the first touch duration is different from the second touch duration; and wherein the illumination of the first portion of the touch surface corresponding to the first touch location is different from the illumination of the second portion of the touch surface corresponding to the second touch location.

5. The method according to claim 3 wherein the first touch duration is at least twice the second touch duration; and wherein the illumination luminosity and/or duration of the first portion of the touch surface corresponding to the first touch location is at least twice the illumination luminosity and/or duration of the second portion of the touch surface corresponding to the second touch location.

6. The method according to claim 5 wherein the illumination duration of the first portion of the touch surface corresponding to the first touch location is at least twice the illumination duration of the second portion of the touch surface corresponding to the second touch location.

7. The method according to claim 5 wherein the illumination luminosity of the first portion of the touch surface corresponding to the first touch location is at least twice the illumination luminosity of the second portion of the touch surface corresponding to the second touch location.

8. A device comprising:
    an ultraviolet pixel array comprising a plurality of pixels that are individually selectable by a controller of the device, each pixel of the array configured to illuminate a portion of the touch surface with an ultraviolet light of a sterilization wavelength; and
    a controller for:
        determining, with the controller, that a touch input has been received at a touch location on a touch surface of the device;
        selecting, with the controller and based upon the touch location, a portion of the touch surface for illumination with ultraviolet light of a sterilization wavelength from at least one pixel of the ultraviolet pixel array, the selected portion being selected to include the touch location;
        selecting to activate the at least one pixel which is less than the plurality of pixels in the ultraviolet pixel array, and to deactivate the remaining pixels in the plurality of pixels conserving power of the device, for illuminating with the activated at least one pixel the selected portion of the touch surface with the ultraviolet light of a sterilization wavelength; and
        illuminating, by the activated at least one pixel of the ultraviolet pixel array, the selected portion of the touch surface with an ultraviolet light of a sterilization wavelength.

9. The device according to claim 8 wherein the controller is configured for performing functions comprising:

determining that the touch input has been received as a swipe gesture in a plurality of touch locations on the touch surface;

selecting, based upon the plurality of touch locations, a plurality of portions of the touch surface that includes the plurality of touch locations, for illumination with ultraviolet light of a sterilization wavelength from at least one pixel of the ultraviolet pixel array;

selecting to activate the at least one pixel which is less than the plurality of pixels, and to deactivate the remaining pixels in the plurality of pixels conserving power of the device, to thereby generate with the activated at least one pixel ultraviolet light of a sterilization wavelength to illuminate the selected plurality of portions of the touch surface; and illuminating, by the activated at least one pixel of the ultraviolet pixel array, the selected portion of the touch surface with an ultraviolet light of a sterilization wavelength.

10. The device according to claim 9 wherein:

the swipe gesture results in receiving the touch input at a first touch location of the plurality of touch locations for a first touch duration and at a second touch location of the plurality of touch locations for a second touch duration;

the selecting of the plurality of portions of the touch surface selects, based upon the first touch location and the second touch location, a first portion of the touch surface for illumination based upon the first touch location of the swipe gesture and selects a second portion of the touch surface for illumination based upon the second touch location of the swipe gesture; and the illuminating modulates luminosity and/or duration of illumination of the first portion of the touch surface based upon the first touch duration, and modulates luminosity and/or duration of the second portion of the touch surface based upon the second touch duration.

11. The device according to claim 10 wherein:

the first touch duration is different from the second touch duration; and the illumination of the first portion of the touch surface corresponding to the first touch location is different from the illumination of the second portion of the touch surface corresponding to the second touch location.

12. The device according to claim 10 wherein:

the first touch duration is at least twice the second touch duration; and the illumination luminosity and/or duration of the first portion of the touch surface corresponding to the first touch location is at least twice the illumination luminosity and/or duration of the second portion of the touch surface corresponding to the second touch location.

13. The device according to claim 12 wherein the illumination duration of the first portion of the touch surface corresponding to the first touch location is at least twice the illumination duration of the second portion of the touch surface corresponding to the second touch location.

14. The device according to claim 12 wherein the illumination luminosity of the first portion of the touch surface corresponding to the first touch location is at least twice the illumination luminosity of the second portion of the touch surface corresponding to the second touch location.

15. The device of claim 8, wherein the device comprises at least one device selected from the following group:

a cell phone;
a tablet;
a personal computer with a touchscreen or touchpad;
a kiosk;
a point of sale system; and
a gaming system.

16. A computer program product comprising:

a non-transitory storage medium readable by a processing circuit and storing instructions for execution by the processing circuit for performing a method comprising:

determining, with the processing circuit, that a touch input has been received at a touch location on a touch surface;

selecting, with the processing circuit and based upon the touch location, a portion of the touch surface for illumination with ultraviolet light of a sterilization wavelength from at least one pixel of an ultraviolet pixel array comprising a plurality of pixels that are individually selectable by the controller, the selected portion being selected to include the touch location;

selecting to activate the at least one pixel which is less than the plurality of pixels, and to deactivate the remaining pixels in the plurality of pixels conserving power of a device, to thereby generate with the activated at least one pixel ultraviolet light of a sterilization wavelength to illuminate the selected portion of the touch surface; and illuminating, by the activated at least one pixel of the ultraviolet pixel array where each pixel of the array is configured to illuminate a portion of the touch surface, the selected portion of the touch surface with an ultraviolet light of a sterilization wavelength.

17. The computer program product according to claim 16, wherein:

the determining that a touch input has been received includes determining that the touch input has been received as a swipe gesture in a plurality of touch locations on the touch surface;

the selecting of a portion of the touch surface selects, based upon the plurality of touch locations, a plurality of portions of the touch surface that includes the plurality of touch locations; and the illuminating illuminates the selected plurality of portions of the touch surface.

18. The computer program product according to claim 17, wherein:

the swipe gesture results in receiving the touch input at a first touch location of the plurality of touch locations for a first touch duration and at a second touch location of the plurality of touch locations for a second touch duration;

the selecting of the plurality of portions of the touch surface selects, based upon the first touch location and the second touch location, a first portion of the touch surface for illumination based upon the first touch location of the swipe gesture and selects a second portion of the touch surface for illumination based upon the second touch location of the swipe gesture; and the illuminating modulates luminosity and/or duration of illumination of the first portion of the touch surface based upon the first touch duration, and modulates luminosity and/or duration of the second portion of the touch surface based upon the second touch duration.

19. The computer program product according to claim 18, wherein:

the first touch duration is different from the second touch duration; and the illumination of the first portion of the touch surface corresponding to the first touch location is different from the illumination of the second portion of the touch surface corresponding to the second touch location.

20. The computer program product according to claim 18, wherein:
the first touch duration is different from the second touch duration; and
the illumination duration of the first portion of the touch surface corresponding to the first touch location is greater than the illumination duration of the second portion of the touch surface corresponding to the second touch location.

* * * * *